US011833301B2

(12) United States Patent
Landis et al.

(10) Patent No.: US 11,833,301 B2
(45) Date of Patent: Dec. 5, 2023

(54) HIGH FLOW THERAPY DEVICE UTILIZING A NON-SEALING RESPIRATORY INTERFACE AND RELATED METHODS

(71) Applicant: ResMed Pty Ltd, Bella Vista (AU)

(72) Inventors: Robert M Landis, Mountainside, NJ (US); Charles A Lewis, Carrabelle, FL (US); Louis Javier Collazo, Pompano Beach, FL (US)

(73) Assignee: ResMed Pty Ltd

( * ) Notice: Subject to any disclaimer, the term of this patent is extended or adjusted under 35 U.S.C. 154(b) by 0 days.

(21) Appl. No.: 15/250,834

(22) Filed: Aug. 29, 2016

(65) Prior Publication Data

US 2016/0367776 A1 Dec. 22, 2016

Related U.S. Application Data

(63) Continuation of application No. 13/717,442, filed on Dec. 17, 2012, now Pat. No. 9,427,547, which is a
(Continued)

(51) Int. Cl.
*A61M 16/10* (2006.01)
*A61M 16/06* (2006.01)
(Continued)

(52) U.S. Cl.
CPC ...... *A61M 16/0069* (2014.02); *A61J 11/0005* (2013.01); *A61M 16/0051* (2013.01);
(Continued)

(58) Field of Classification Search
CPC ..... A61B 5/0205; A61B 5/0816; A61B 5/087; A61B 5/14551; A61B 5/4818;
(Continued)

(56) References Cited

U.S. PATENT DOCUMENTS 3,181,895 A  5/1965  Cator
3,295,521 A * 1/1967  Balch ................. A61M 16/06
                                                      128/206.28
(Continued)

FOREIGN PATENT DOCUMENTS

DE  3708146 A1  9/1988
FR  2827778 A1  1/2003
(Continued)

OTHER PUBLICATIONS

Final Office Action dated Dec. 14, 2020 for U.S. Appl. No. 14/016,042, 22 pages.
(Continued)

*Primary Examiner* — Annette Dixon
(74) *Attorney, Agent, or Firm* — Botos Churchill IP Law LLP

(57) ABSTRACT

A high flow therapy system for delivering heated and humidified respiratory gas to an airway of a patient includes a respiratory gas flow pathway for delivering the respiratory gas to the airway of the patient by way of a non-sealing respiratory interface; wherein flow rate of the respiratory gas is controlled by a microprocessor, a mixing area for mixing a first gas and a second gas in the respiratory gas flow pathway, a humidification area downstream of the mixing area and configured for humidifying respiratory gas in the respiratory gas flow pathway, and a heated delivery conduit for minimizing condensation of humidified respiratory gas.

25 Claims, 23 Drawing Sheets

Related U.S. Application Data continuation of application No. 11/638,981, filed on Dec. 14, 2006, now Pat. No. 8,333,194, which is a continuation-in-part of application No. 11/520,490, filed on Sep. 12, 2006, now abandoned.

(60) Provisional application No. 60/716,776, filed on Sep. 12, 2005, provisional application No. 60/792,711, filed on Apr. 18, 2006, provisional application No. 60/750,063, filed on Dec. 14, 2005.

(51) Int. Cl.
| | | |
|---|---|---|
| *A61M 16/00* | (2006.01) | |
| *A61M 16/04* | (2006.01) | |
| *A61M 16/08* | (2006.01) | |
| *A61M 16/12* | (2006.01) | |
| *A61M 16/14* | (2006.01) | |
| *A61M 16/20* | (2006.01) | |
| *A61J 11/00* | (2006.01) | |
| *A61M 16/16* | (2006.01) | |
| *A61M 16/18* | (2006.01) | |

(52) U.S. Cl.
CPC .... *A61M 16/0057* (2013.01); *A61M 16/0493* (2014.02); *A61M 16/0666* (2013.01); *A61M 16/0677* (2014.02); *A61M 16/085* (2014.02); *A61M 16/0858* (2014.02); *A61M 16/107* (2014.02); *A61M 16/109* (2014.02); *A61M 16/1075* (2013.01); *A61M 16/1095* (2014.02); *A61M 16/12* (2013.01); *A61M 16/125* (2014.02); *A61M 16/142* (2014.02); *A61M 16/16* (2013.01); *A61M 16/20* (2013.01); *A61M 16/203* (2014.02); *A61M 16/0066* (2013.01); *A61M 16/18* (2013.01); *A61M 2016/0024* (2013.01); *A61M 2016/0027* (2013.01); *A61M 2016/103* (2013.01); *A61M 2016/1025* (2013.01); *A61M 2202/0208* (2013.01); *A61M 2205/18* (2013.01); *A61M 2205/3334* (2013.01); *A61M 2205/3368* (2013.01); *A61M 2205/3653* (2013.01); *A61M 2205/50* (2013.01); *A61M 2230/005* (2013.01); *A61M 2230/42* (2013.01); *A61M 2230/432* (2013.01); *A61M 2230/435* (2013.01); *A61M 2230/50* (2013.01)

(58) Field of Classification Search
CPC ...... A61B 5/6819; A61D 7/04; A61J 11/0005; A61J 17/001; A61J 17/006; A61J 7/0053; A61M 16/00; A61M 16/0051; A61M 16/0057; A61M 16/0063; A61M 16/0066; A61M 16/0069; A61M 16/0488; A61M 16/049; A61M 16/0493; A61M 16/0666; A61M 16/0672; A61M 16/0677; A61M 16/08; A61M 16/0816; A61M 16/0825; A61M 16/0833; A61M 16/085; A61M 16/0858; A61M 16/101; A61M 16/105; A61M 16/107; A61M 16/1075; A61M 16/108; A61M 16/1085; A61M 16/109; A61M 16/1095; A61M 16/12; A61M 16/122; A61M 16/125; A61M 16/142; A61M 16/16; A61M 16/161; A61M 16/18; A61M 16/20; A61M 16/203; A61M 2016/0021; A61M 2016/0024; A61M 2016/0027; A61M 2016/0039; A61M 2016/1025; A61M 2016/103; A61M 2202/0208; A61M 2205/18; A61M 2205/3334; A61M 2205/3368; A61M 2205/3382; A61M 2205/3386; A61M 2205/3561; A61M 2205/3592; A61M 2205/3633; A61M 2205/3653; A61M 2205/42; A61M 2205/50; A61M 2205/502; A61M 2205/52; A61M 2205/581; A61M 2205/582; A61M 2205/583; A61M 2230/005; A61M 2230/42; A61M 2230/432; A61M 2230/435; A61M 2230/50; A61M 16/0003; A61M 16/0078; A61M 16/024; A61M 16/06; A61M 16/0627; A61M 16/0683; A61M 16/0841; A61M 16/10; A61M 16/1015; A61M 16/1045; A61M 16/162; A61M 16/202; A61M 16/205; A61M 16/206; A61M 16/208; A61M 16/209; A61M 2016/0036; A61M 2016/0042; A61M 2016/0208; A61M 2205/123; A61M 2205/16; A61M 2205/3331; A61M 2205/3355; A61M 2205/3358; A61M 2205/3365; A61M 2205/3553; A61M 2205/3569; A61M 2205/3584; A61M 2205/505; A61M 2205/587; A61M 2205/70; A61M 2205/8206; A61M 2205/8212; A61M 2209/086; A61M 2230/205; A61M 2230/46; Y10S 261/31; Y10S 261/65; A61G 10/005; A61G 10/023; A61G 13/108; A62B 31/00; A62B 7/02; G01F 1/40; G01F 1/42; G01F 1/684; G01F 1/6842; G01F 1/6888; G08B 21/16

USPC ............ 128/200.24, 200.26, 203.16, 203.17, 128/203.26, 203.27, 204.14, 204.17, 128/204.18, 204.21, 204.23, 206.29, 128/207.18; 261/DIG. 31; 600/561

See application file for complete search history.

(56) References Cited

U.S. PATENT DOCUMENTS

| | | | |
|---|---|---|---|
| 3,807,445 A | 4/1974 | McPhee | |
| 3,863,630 A | 2/1975 | Cavallo | |
| 3,864,440 A | 2/1975 | Giocoechea | |
| 3,913,843 A | 10/1975 | Cambio | |
| 4,060,576 A | 11/1977 | Grant | |
| 4,109,509 A | 8/1978 | Cramer et al. | |
| 4,203,027 A | 5/1980 | Brickell et al. | |
| 4,260,180 A | 4/1981 | Halushka et al. | |
| 4,399,349 A | 8/1983 | Deming et al. | |
| 4,444,183 A * | 4/1984 | Heckendorn ..... | A61M 16/0627 128/204.18 |
| 4,535,767 A * | 8/1985 | Tiep ................. | A61M 16/0666 128/205.17 |
| 4,621,632 A | 11/1986 | Bartels et al. | |
| 4,682,010 A | 7/1987 | Drapeau et al. | |
| 4,708,831 A | 11/1987 | Elsworth et al. | |
| 4,722,334 A * | 2/1988 | Blackmer ............. | A61D 7/04 128/203.16 |
| 4,753,233 A | 6/1988 | Grimes | |
| 4,807,616 A | 2/1989 | Adahan | |
| 4,838,258 A | 6/1989 | Dryden et al. | |
| 4,913,140 A | 4/1990 | Orec et al. | |
| 4,941,469 A | 7/1990 | Adahan | |
| 4,967,744 A | 11/1990 | Chua | |
| 5,031,612 A | 7/1991 | Clementi | |
| 5,099,836 A | 3/1992 | Rowland et al. | |
| 5,139,741 A | 8/1992 | Hagiwara | |
| 5,195,515 A | 3/1993 | Levine | |
| 5,226,411 A | 7/1993 | Levine | |
| 5,237,987 A | 8/1993 | Anderson et al. | |
| 5,239,994 A | 8/1993 | Atkins | |

(56) References Cited

U.S. PATENT DOCUMENTS

| | | | |
|---|---|---|---|
| 5,284,160 A | 2/1994 | Dryden | |
| 5,394,881 A | 3/1995 | Block | |
| 5,445,143 A | 8/1995 | Sims | |
| 5,495,848 A | 3/1996 | Aylsworth et al. | |
| 5,503,146 A | 4/1996 | Froehlich et al. | |
| 5,551,419 A | 9/1996 | Froehlich et al. | |
| 5,588,423 A | 12/1996 | Smith | |
| 5,640,951 A | 6/1997 | Huddart et al. | |
| 5,682,877 A * | 11/1997 | Mondry | A61M 16/0627 128/204.23 |
| 5,692,497 A * | 12/1997 | Schnitzer | A61M 16/00 128/204.18 |
| 5,720,276 A | 2/1998 | Kobatake et al. | |
| 5,743,253 A * | 4/1998 | Castor | A61M 16/00 128/200.24 |
| 5,752,506 A | 5/1998 | Richardson | |
| 5,832,919 A * | 11/1998 | Kano | A61G 10/005 128/205.26 |
| 5,868,133 A * | 2/1999 | DeVries | A61M 16/125 128/204.18 |
| 5,950,621 A | 9/1999 | Klockseth et al. | |
| 5,954,050 A * | 9/1999 | Christopher | A61M 16/00 128/204.18 |
| 6,010,118 A | 1/2000 | Milewicz | |
| 6,093,169 A | 7/2000 | Cardoso | |
| 6,150,661 A | 11/2000 | McCaul et al. | |
| 6,155,986 A | 12/2000 | Brydon et al. | |
| 6,213,955 B1 | 4/2001 | Karakasoglu et al. | |
| 6,272,933 B1 * | 8/2001 | Gradon | G08B 21/16 73/861 |
| 6,516,800 B1 | 2/2003 | Bowden | |
| 6,533,984 B2 | 3/2003 | Curti | |
| 6,536,432 B2 | 3/2003 | Truschel | |
| 6,571,794 B1 | 6/2003 | Hansen | |
| 6,595,215 B2 | 7/2003 | Wood | |
| 6,626,175 B2 | 9/2003 | Jafari et al. | |
| 6,655,385 B1 | 12/2003 | Curti et al. | |
| 7,007,692 B2 | 3/2006 | Aylsworth et al. | |
| 7,007,694 B2 | 3/2006 | Aylsworth et al. | |
| 7,043,979 B2 | 5/2006 | Smith et al. | |
| 7,051,733 B2 | 5/2006 | Gradon et al. | |
| 7,086,399 B2 | 8/2006 | Makinson et al. | |
| 7,106,955 B2 | 9/2006 | Thudor et al. | |
| 7,114,497 B2 | 10/2006 | Aylsworth et al. | |
| 7,152,604 B2 | 12/2006 | Hickle et al. | |
| 7,380,551 B2 | 6/2008 | Alvey | |
| 7,520,277 B1 * | 4/2009 | Grady | A61M 16/0833 128/201.23 |
| 7,543,584 B2 | 6/2009 | Brookman | |
| 8,220,458 B2 | 7/2012 | Landis et al. | |
| 8,267,084 B2 | 9/2012 | Kwok | |
| 8,333,194 B2 * | 12/2012 | Lewis | A61J 11/0005 128/200.24 |
| RE44,453 E | 8/2013 | Virr et al. | |
| 8,522,782 B2 | 9/2013 | Lewis et al. | |
| 9,427,547 B2 * | 8/2016 | Landis | A61J 11/0005 |
| 10,449,320 B2 | 10/2019 | Miller et al. | |
| 10,617,835 B2 | 4/2020 | Schermeier et al. | |
| 10,737,049 B1 | 8/2020 | Orr et al. | |
| 10,828,482 B2 | 11/2020 | Osborne et al. | |
| 11,071,464 B2 | 7/2021 | Landis et al. | |
| 11,406,777 B2 | 8/2022 | Landis et al. | |
| 2001/0017134 A1 | 8/2001 | Bahr | |
| 2002/0005201 A1 | 1/2002 | Gradon et al. | |
| 2002/0053286 A1 | 5/2002 | Czabala | |
| 2002/0053345 A1 | 5/2002 | Jafari et al. | |
| 2002/0053346 A1 | 5/2002 | Curti et al. | |
| 2002/0055685 A1 * | 5/2002 | Levitsky | A61M 16/085 128/207.18 |
| 2002/0059935 A1 * | 5/2002 | Wood | A61M 16/0666 128/207.18 |
| 2002/0078958 A1 * | 6/2002 | Stenzler | A61M 16/026 128/207.14 |
| 2002/0100320 A1 | 8/2002 | Smith et al. | |
| 2003/0111079 A1 | 6/2003 | Matthews et al. | |
| 2003/0111080 A1 | 6/2003 | Olsen et al. | |
| 2004/0065335 A1 | 4/2004 | Huber et al. | |
| 2004/0182392 A1 | 9/2004 | Gerder et al. | |
| 2005/0178383 A1 | 8/2005 | Mackie et al. | |
| 2005/0199242 A1 | 9/2005 | Matula et al. | |
| 2006/0042631 A1 | 3/2006 | Martin et al. | |
| 2006/0118111 A1 | 6/2006 | Pelerossi et al. | |
| 2006/0219245 A1 | 10/2006 | Holder | |
| 2007/0107737 A1 | 5/2007 | Landis et al. | |
| 2007/0169776 A1 * | 7/2007 | Kepler | A61M 16/109 128/200.23 |
| 2007/0175473 A1 | 8/2007 | Lewis et al. | |
| 2008/0051674 A1 * | 2/2008 | Davenport | A61B 5/087 600/561 |
| 2008/0142019 A1 | 6/2008 | Lewis et al. | |
| 2008/0308100 A1 | 12/2008 | Pujol et al. | |
| 2009/0101147 A1 | 4/2009 | Landis et al. | |
| 2013/0340752 A1 | 12/2013 | Landis et al. | |
| 2016/0367776 A1 | 12/2016 | Landis et al. | |
| 2016/0367779 A1 | 12/2016 | Landis et al. | |
| 2017/0304570 A1 | 10/2017 | Landis et al. | |
| 2021/0353158 A1 | 11/2021 | Landis et al. | |
| 2021/0353159 A1 | 11/2021 | Landis et al. | |
| 2021/0353885 A1 | 11/2021 | Landis et al. | |
| 2022/0031173 A1 | 2/2022 | Landis et al. | |

FOREIGN PATENT DOCUMENTS

| | | |
|---|---|---|
| WO | 2004105846 A2 | 12/2004 |
| WO | 2004112873 A1 | 12/2004 |
| WO | 2005011785 A1 | 2/2005 |
| WO | 2005018724 A1 | 3/2005 |
| WO | 2005055809 A2 | 6/2005 |
| WO | 2006056445 A1 | 6/2006 |
| WO | 2006125252 A1 | 11/2006 |
| WO | 2006126900 A1 | 11/2006 |

OTHER PUBLICATIONS

Final Office Action dated Dec. 24, 2020 for U.S. Appl. No. 14/016,042.
International Search Report and Written Opinion for International Application No. PCT/US2007/025085, dated Apr. 24, 2008, 8 pages.
International Search Report and Written Opinion from PCT/US2006/035947, dated Apr. 13, 2007, 15 pages.
Non Final Office Action dated Dec. 2, 2021 for U.S. Appl. No. 17/387,505.
Final Office Action dated Mar. 22, 2022 for U.S. Appl. No. 17/387,657.
International Search Report from PCT/US2006/035947 dated Dec. 22, 2006, 5 pages.
Non Final Office Action dated Nov. 15, 2021 for U.S. Appl. No. 17/387,538.
Notice of Allowance dated Mar. 15, 2022 for U.S. Appl. No. 17/387,538.
Notice of Allowance dated Mar. 28, 2022 for U.S. Appl. No. 17/387,752.
Notice of Allowance dated Mar. 30, 2022 for U.S. Appl. No. 17/387,505.

* cited by examiner

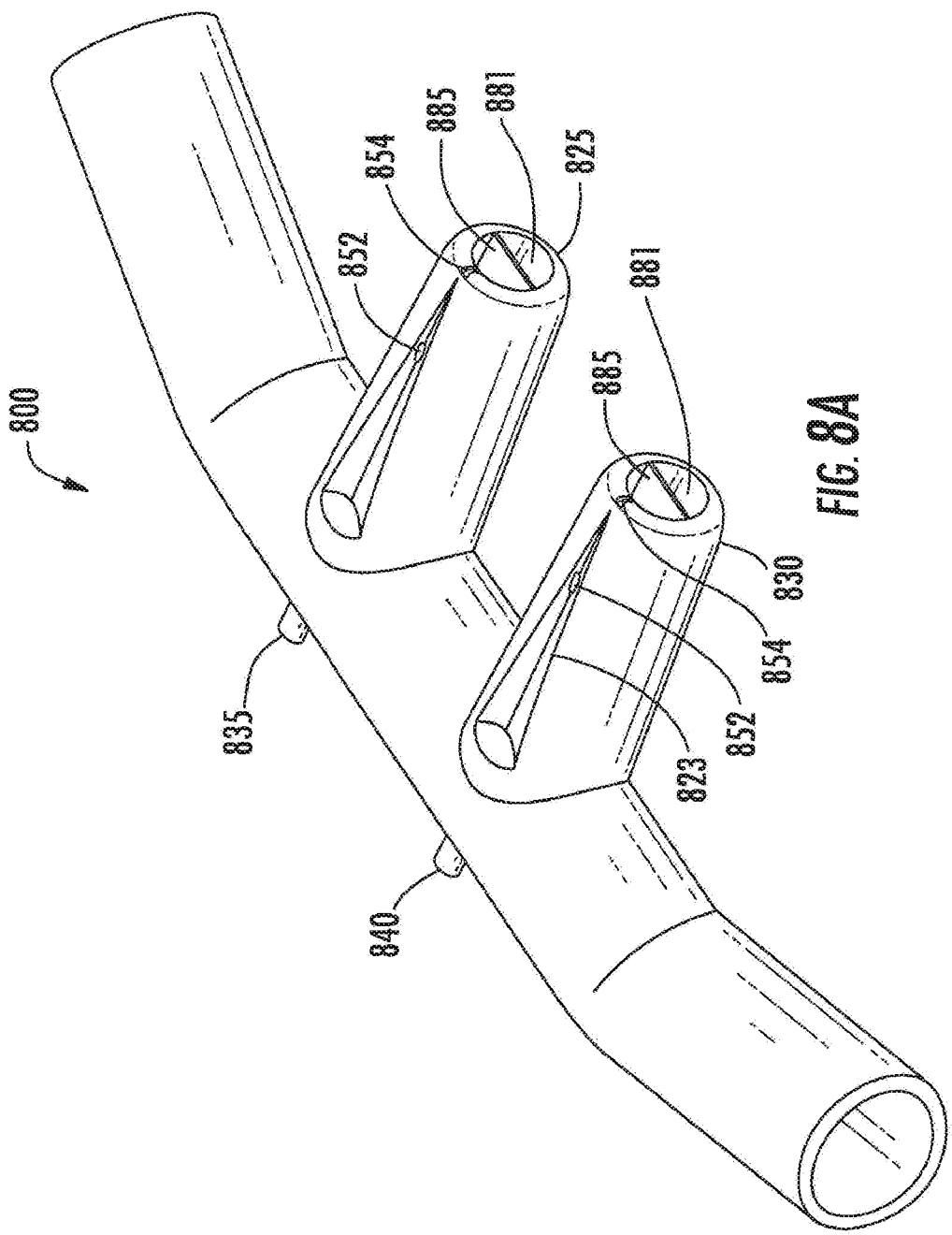

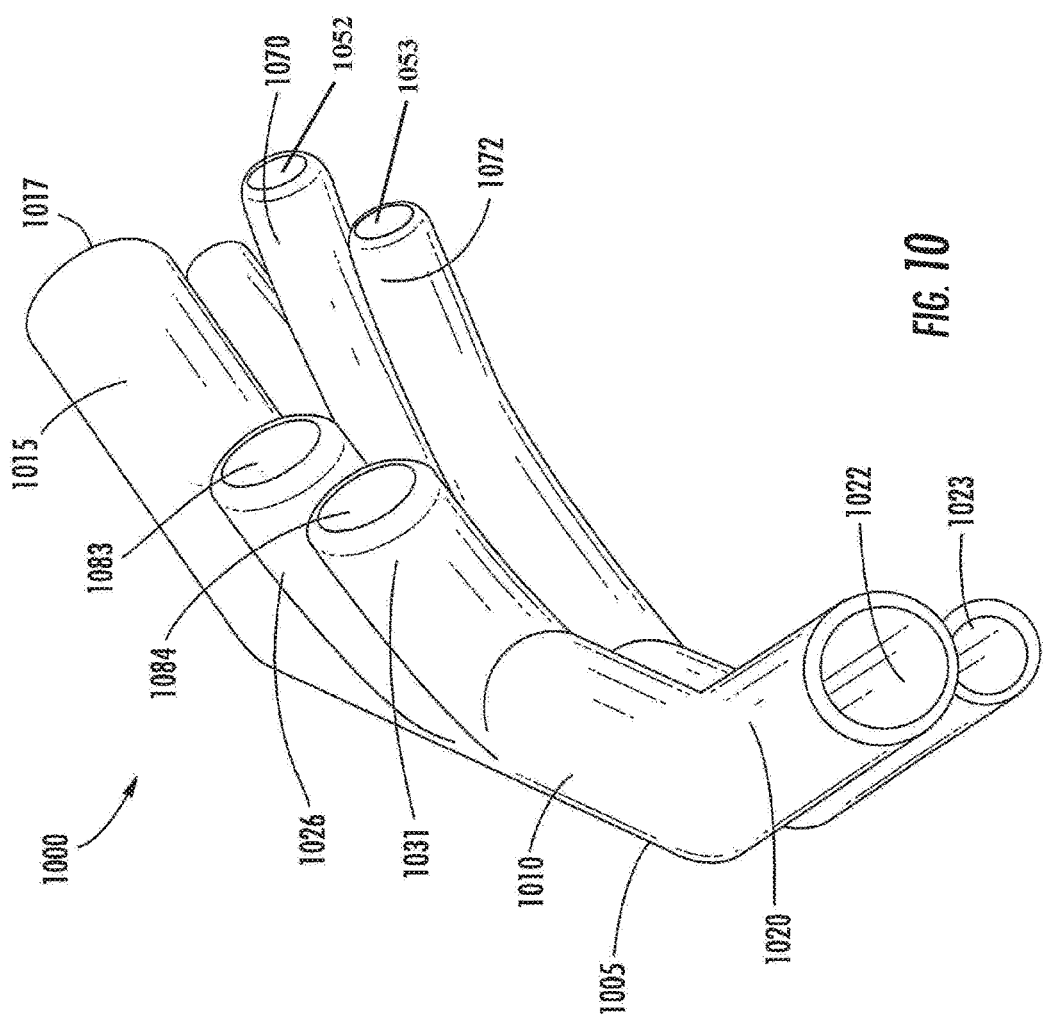

HIGH FLOW THERAPY DEVICE UTILIZING A NON-SEALING RESPIRATORY INTERFACE AND RELATED METHODS

CROSS-REFERENCE TO RELATED APPLICATIONS

This application is a continuation application of U.S. patent application Ser. No. 13/717,442, filed on Dec. 17, 2012, which is a continuation application of U.S. patent application Ser. No. 11/638,981, filed on Dec. 14, 2006, now U.S. Pat. No. 8,333,194, which is a continuation-in-part application of U.S. patent application Ser. No. 11/520,490, filed on Sep. 12, 2006, which claims the benefit of U.S. Provisional Patent Application Ser. No. 60/716,776, filed Sep. 12, 2005. The present application also claims the benefit and priority of U.S. Provisional Patent Application Ser. No. 60/750,063, filed on Dec. 14, 2005; U.S. Provisional Patent Application Ser. No. 60/792,711, filed on Apr. 18, 2006; and U.S. Provisional Patent Application Ser. No. 60/852,851, filed on Oct. 18, 2006. The entire contents of each of these applications are hereby incorporated by reference herein.

BACKGROUND

Respiratory interfaces, e.g., nasal cannulas are used to deliver respiratory gases for therapeutic effect, including oxygen therapy, treatment for sleep apnea, and respiratory support. Small nasal cannulas are commonly used for delivery of low volumes of oxygen. Sealing nasal cannulas, such as the cannulas disclosed in U.S. Pat. No. 6,595,215 to Wood, are used for the treatment of sleep apnea. However, treatment with certain types of nasal cannulas may be limited by the lack of information available on important treatment parameters. These parameters include information regarding the gases within the user's upper airway, such as pressure, flow rate, and carbon dioxide build up. These and other data may be useful in judging the efficacy of treatment as well as for controlling and monitoring treatment.

In addition, prior art nasal cannula designs (especially those designed for neonatal oxygen therapy) may undesirably create a seal with the user's nares, which may have detrimental effects on the user's health.

Oxygen ($O_2$) therapy is often used to assist and supplement patients who have respiratory impairments that respond to supplemental oxygen for recovery, healing and also to sustain daily activity.

Nasal cannulas are generally used during oxygen therapy. This method of therapy typically provides an air/gas mixture including about 24% to about 35% $O_2$ at flow rates of 1-6 liters per minute (L/min). At around two liters per minute, the patient will have a $FiO_2$ (percent oxygen in the inhaled $O_2$/air mixture) of about 28% oxygen. This rate may be increase somewhat to about 8 L/min if the gas is passed through a humidifier at room temperature via a nasal interface into the patient's nose. This is generally adequate for many people whose condition responds to about 35-40% inhaled $O_2$ ($FiO_2$), but for higher concentrations of $O_2$, higher flow rates are generally needed.

When a higher $FiO_2$ is needed, one cannot simply increase the flow rate. This is true because breathing 100% $O_2$ at room temperature via a nasal cannula is irritating to the nasal passage and is generally not tolerated above about 7-8 L/min. Simply increasing the flow rate may also provoke bronchospasm.

To administer $FiO_2$ of about 40% to about 100%, non-rebreathing masks (or sealed masks) are used at higher flows. The mask seals on the face and has a reservoir bag to collect the flow of oxygen during the exhalation phase and utilize one-way directional valves to direct exhalation out into the room and inhalation from the oxygen reservoir bag. This method is mostly employed in emergency situations and is generally not tolerated well for extended therapy.

High flow nasal airway respiratory support ("high flow therapy" or "HFT") is administered through a nasal cannula into an "open" nasal airway. The airway pressures are generally lower than Continuous Positive Airway Pressure (CPAP) and Bi-level Positive Airway Pressure (BiPAP) and are not monitored or controlled. The effects of such high flow therapies are reported as therapeutic and embraced by some clinicians while questioned by others because it involves unknown factors and arbitrary administration techniques. In such procedures, the pressures generated in the patients' airways are typically variable, affected by cannula size, nare size, flow rate, and breathing rate, for instance. It is generally known that airway pressures affect oxygen saturation, thus these variables are enough to keep many physicians from utilizing HFT.

SUMMARY

The present disclosure relates to a high flow therapy system for delivering heated and humidified respiratory gas to an airway of a patient includes a respiratory gas flow pathway for delivering the respiratory gas to the airway of the patient by way of a non-sealing respiratory interface; wherein flow rate of the respiratory gas is controlled by a microprocessor, a mixing area for mixing a first gas and a second gas in the respiratory gas flow pathway, a humidification area downstream of the mixing area and configured for humidifying respiratory gas in the respiratory gas flow pathway, and a heated delivery conduit for minimizing condensation of humidified respiratory gas. Another aspect of this embodiment provides for at least one of respiration rate, tidal volume and minute volume are calculated by the microprocessor using data from the airway pressure sensor.

The present disclosure also relates to a method of supplying a patient with gas. The method includes providing a high flow therapy device including a microprocessor, a heating element disposed in electrical communication with the microprocessor and capable of heating a liquid to create a gas, a non-sealing respiratory interface configured to deliver the gas to a patient and a sensor disposed in electrical communication with the microprocessor and configured to measure pressure in the upper airway of the patient. This method also includes heating the gas and delivering the gas to a patient.

The present disclosure also relates to a high flow therapy system for delivering pressurized, heated and humidified respiratory gas to an airway of a patient includes a respiratory gas flow pathway for delivering the pressurized respiratory gas to the airway of the patient by way of a non-sealing respiratory interface; where flow rate of the pressurized respiratory gas is controlled by a microprocessor, a mixing area for mixing oxygen and air in the respiratory gas flow pathway, a humidification area for humidifying respiratory gas in the respiratory gas flow pathway, a heated delivery conduit for minimizing condensation of humidified respiratory gas and a pressure pathway for monitoring pressure of the airway of the patient and communicating the monitored pressure to the microprocessor, where the system is configured to determine the respiratory phase of the patient.

The present disclosure also relates to a method of supplying a patient with gas. The method including providing a high flow therapy device, heating a gas and delivering the gas to a patient. The high flow therapy device of this method includes a heating element, a non-sealing respiratory interface, a blower, an air inlet port and an air filter. The heating element is capable of heating a liquid to create a gas. The non-sealing respiratory interface is configured to deliver the gas to a patient. The blower is dispose din mechanical cooperation with the non-sealing respiratory interface and is capable of advancing the gas at least partially through the non-sealing respiratory interface. The air inlet port is configured to enable ambient air to flow towards to the blower. The air filter is disposed in mechanical cooperation with the air inlet port and is configured to remove particulates from the ambient air.

The present disclosure also relates to a method of treating a patient for an ailment such as a headache, upper airway resistance syndrome, obstructive sleep apnea, hypopnea and snoring. The method includes providing a high flow therapy device, heating a gas and delivering the gas to a patient. The high flow therapy device includes a heating element capable of heating a liquid to create a gas and a non-sealing respiratory interface configured to deliver the gas to a patient.

The present disclosure also relates to a method of delivering respiratory gas to a patient. The method includes providing a high flow therapy device, monitoring the respiratory phase of the patient and pressurizing the gas. The high flow therapy device of this method includes a heating element capable of heating a liquid to create a gas, a non-sealing respiratory interface configured to deliver the gas to a patient, and a sensor configured to measure pressure in the upper airway of the patient.

The present disclosure also relates to a high flow therapy device including a microprocessor, a heating element, a non-sealing respiratory interface, a sensor and a mouthpiece. The heating element is disposed in electrical communication with the microprocessor and is capable of heating a liquid to create a gas. The non-sealing respiratory interface is configured to deliver the gas to a patient. The sensor is disposed in electrical communication with the microprocessor and is configured to measure pressure in an upper airway of the patient. The mouthpiece is disposed in mechanical cooperation with the sensor.

BRIEF DESCRIPTION OF THE DRAWINGS

Reference will now be made to the accompanying drawing figures, which are not necessarily drawn to scale.

FIG. 8A is a front perspective view of a nasal cannula according to another embodiment of the invention.

FIG. 10 is a perspective view of a nasal cannula according to another embodiment of the invention.

FIG. 11 is a perspective view of a nasal cannula according to a further embodiment of the invention.

DETAILED DESCRIPTION OF THE INVENTION

Figure 1:
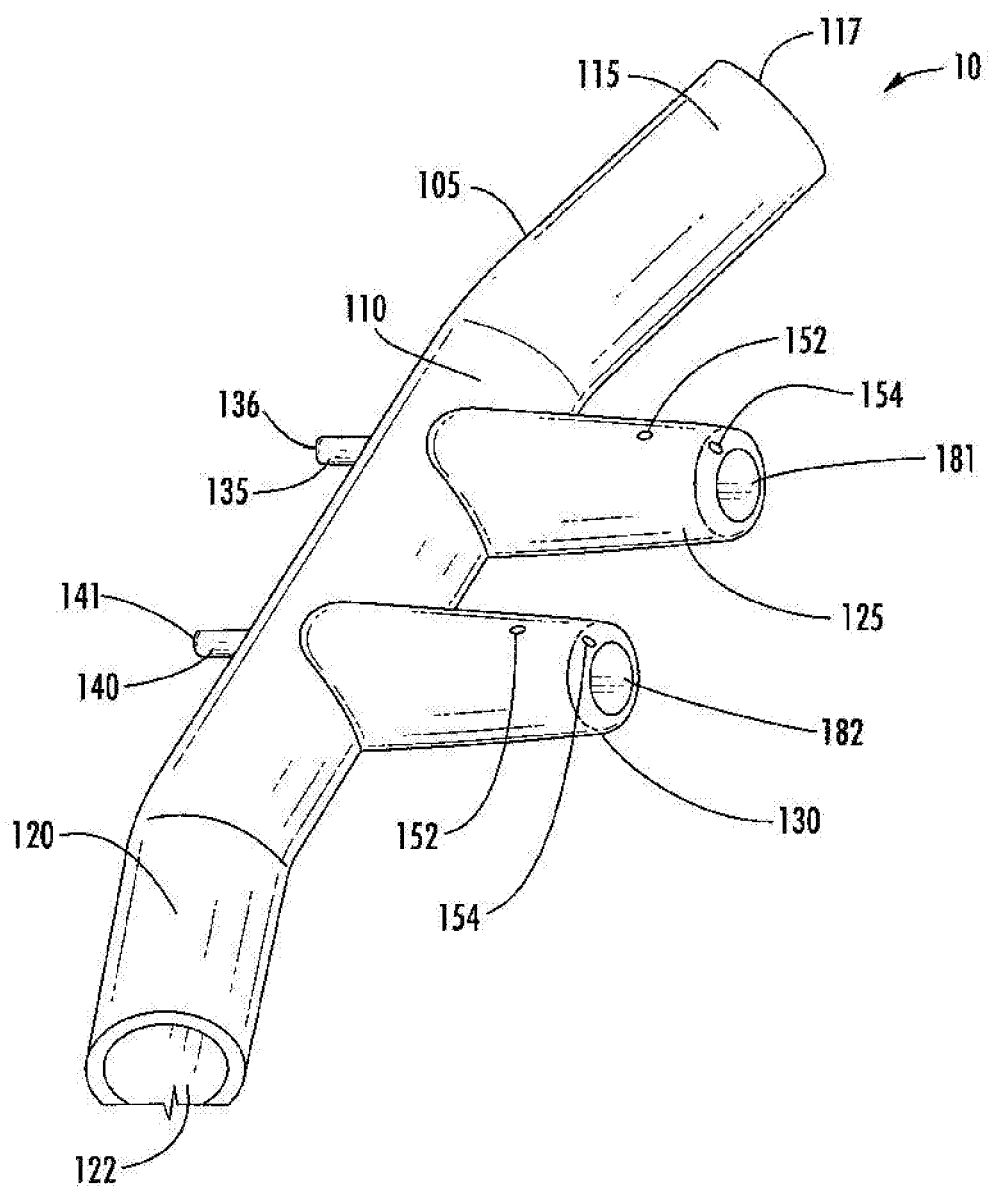
FIG. 1 is a perspective view of a nasal cannula according to a particular embodiment of the invention.

The present inventions now will be described with reference to the accompanying drawings, in which some, but not all embodiments of the inventions are shown. Indeed, these inventions may be embodied in many different forms and should not be construed as limited to the embodiments set forth herein. Rather, these embodiments are provided so that this disclosure will satisfy applicable legal requirements. Like numbers refer to like elements throughout. For example, elements 130, 230, 330, 430, 530, 830, and 930 are all nozzles according to various embodiments of the invention.

Overview of Functionality

Nasal cannula according to various embodiments of the invention may be configured to deliver high-flow therapeutic gases to a patient's upper airway through the patient's nose. Such gases may include, for example, air, humidity, oxygen, therapeutic gases or a mixture of these, and may be heated or unheated. In particular embodiments of the invention, the cannula may be useful for CPAP (continuous positive airway pressure) applications, which may be useful in the treatment of sleep apnea and in providing respiratory support to patients (e.g., after abdominal surgery), to alleviate snoring, or for other therapeutic uses.

Nasal cannula according to particular embodiments of the invention include (or are adapted to facilitate the positioning of) one or more sensors adjacent or within one or more of the cannula's nasal inserts. Accordingly, the nasal cannula may be configured so that at least a portion of one or more sensors is in place in one or both of a user's nares when the nasal cannula is operably worn by the user. This may be particularly helpful in evaluating the environment of the internal portion of the user's nose and/or the user's upper airway. As described in greater detail below, in various embodiments of the invention, the cannula is adapted so that it will not create a seal with the patient's nares when the cannula is in use.

Nasal cannula according to other embodiments of the invention include nozzles. A nozzle may be a nasal insert that is inserted into the user's nares. Other nozzles are adapted to remain outside of a user's nares while the cannula is in use. Accordingly, the nozzles avoid sealing with the patient's nares while the cannula is in use. In some embodiments, the nasal cannula include elongate extensions that are inserted into the user's nares to detect pressure in one or both nares.

In certain embodiments of the invention, sensors are provided adjacent or within both of the nasal cannula's nozzles. In various other embodiments, sensors are provided adjacent or within one or more elongate extensions that extend into the user's nares. In various embodiments, elongate extensions may be used in conjunction with nasal inserts or with nozzles. The use of sensors may be useful, for example, in monitoring environmental changes from one of the user's nares to the other. This information may be helpful, for example, in determining when the dominant flow of air changes from one of the user's nares to the other, which may affect the desired flow characteristics of therapy. Accordingly, data from each nare may provide information that may be useful in establishing or modifying the user's treatment regimen. Further, multiple sensors may be used in various embodiments.

Overview of Exemplary Cannula Structures

A cannula 10 according to one embodiment of the invention is shown in FIG. 1. As may be understood from this figure, in this embodiment, the cannula 10 includes a base portion 105, which is hollow, elongated, and tubular that includes a central portion 110, a first end portion 115, and a second end portion 120. The first and second end portions 115, 120 may be angled relative to the central portion 110 as shown in FIG. 1.

In various embodiments of the invention, the cannula 10 includes a first tubing inlet 117 adjacent the outer end of the first end portion 115, and a second tubing inlet 122 adjacent the second end portion 120 (in other embodiments, the cannula may include only one such inlet). The cannula 10 further comprises a pair of hollow, elongated, tubular nozzles (e.g., nasal catheters), nozzles 125, 130, that extend outwardly from the base portion 105 and that are in gaseous communication with the base portion's interior. In various embodiments, the respective central axes of the nozzles 125, 130 are substantially parallel to each other, and are substantially perpendicular to the central axis of the central portion 110 of the base portion 105.

In particular embodiments of the invention, the cannula defines at least one conduit that is adapted to guide at least one sensor so that the sensor is introduced adjacent or into the interior of the cannula so that, when the cannula is being operably worn by a user, the environment being monitored by the at least one sensor reflects that of the internal portion of the user's nose and/or the user's upper airway. In various embodiments of the invention, a user may temporarily insert the at least one sensor into or through the conduit to determine correct settings for the cannula system, and then may remove the sensor after the correct settings have been achieved. In other embodiments, the at least one sensor may be left in place within the conduit for the purpose of monitoring data within (or adjacent) the cannula over time (e.g., for purposes of controlling the user's therapy regimen). In a further embodiment, the at least one sensor may be positioned adjacent an outlet of the conduit.

The at least one sensor may be connected (e.g., via electrical wires) to a computer and/or a microprocessor that is controlling the flow of respiratory gases into the cannula. The computer may use information received from the at least one sensor to control this flow of gas and/or other properties of the system, or may issue an alarm if the information satisfies pre-determined criteria (e.g., if the information indicates potentially dangerous conditions within the patient's airway or if the system fails to operate correctly).

Figure 8B:
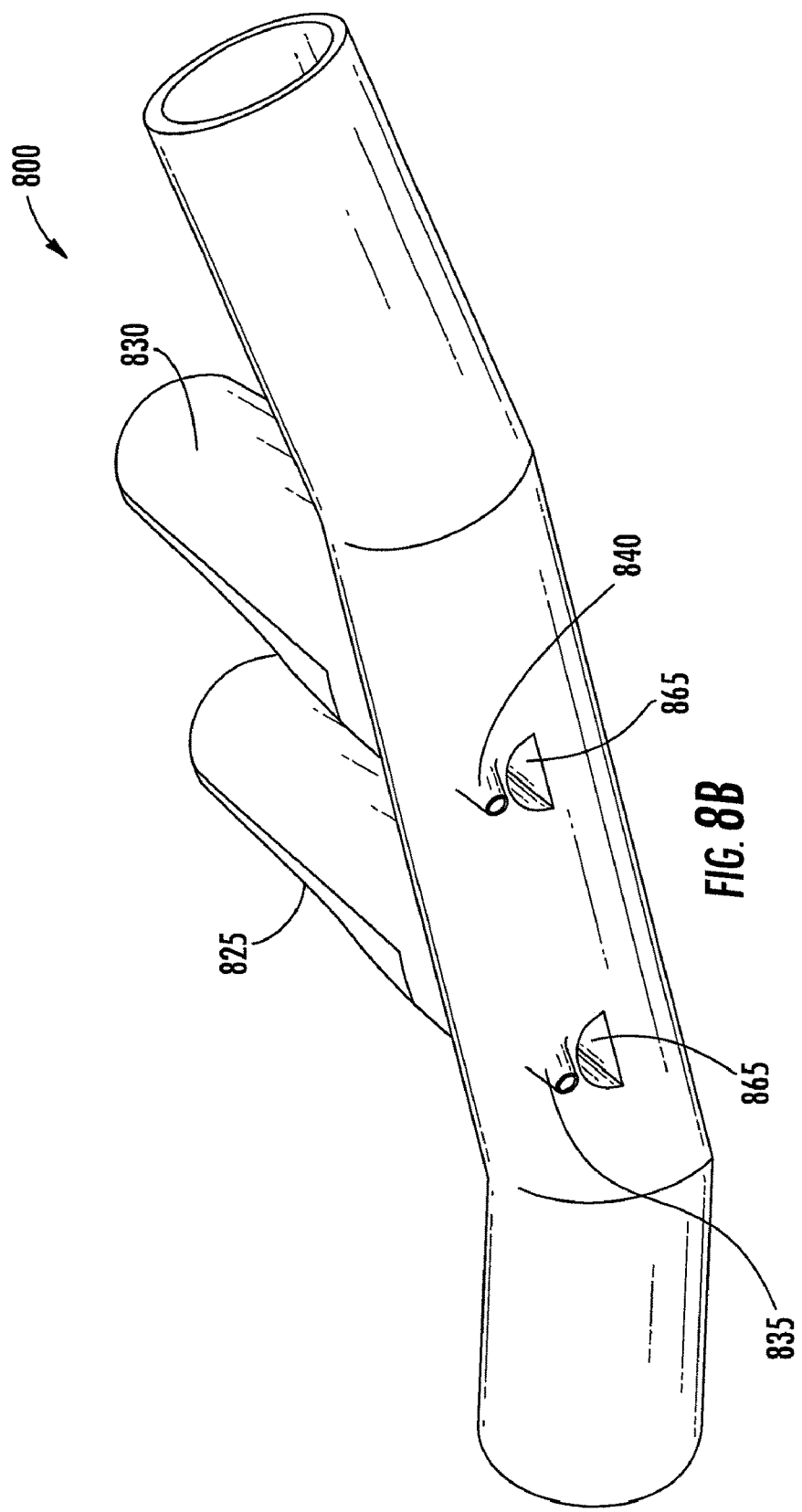
FIG. 8B is a rear perspective view of the nasal cannula shown in FIG. 8A.
Figure 8C:
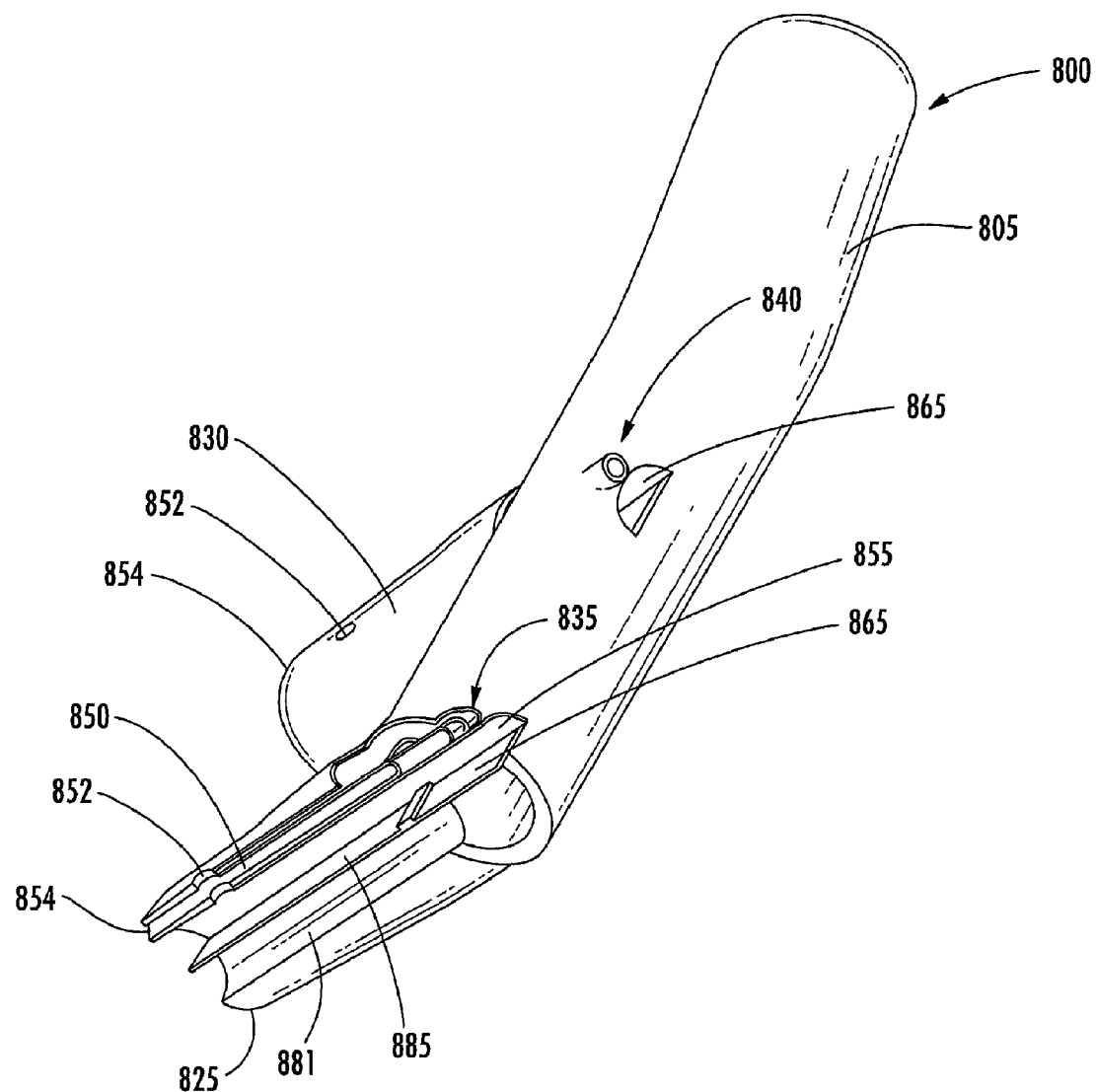
FIG. 8C is a perspective cross-sectional view of the nasal cannula shown in FIG. 8A.

As may be understood from FIGS. 8A-8C, in a particular embodiment of the invention, at least one of the cannula's conduits 850 is defined by, and extends within, a side wall of the cannula 800. Alternatively, the conduit may be disposed within an interior passage defined by the cannula. For example, one or more of the conduits may be defined by a tube that is attached immediately adjacent an interior surface of the cannula (e.g., adjacent an interior surface of the cannula's base portion, or an interior surface of one of the cannula's nozzles). The cannula's conduits are preferably adapted for: (1) receiving a flow of gas at one or more inlets that are in communication with the conduit, and (2) guiding this flow of gas to an outlet in the cannula. In various embodiments, one or more of the inlets is defined within an exterior portion of one of the cannula's nozzles.

As may be understood from FIG. 1, in various embodiments of the invention, each of the cannula's conduit outlets 136, 141 is located at the end of a respective elongate, substantially tubular, outlet member 135, 140. For example, in the embodiment shown in FIG. 1, the cannula 10 includes a first outlet member 135 that is substantially parallel to the cannula's first nozzle 125. In this embodiment, the first outlet member 135 and the first nozzle 125 may be positioned on opposite sides of the base portion 105 as shown in FIG. 1. Similarly, in a particular embodiment of the invention, the cannula 10 includes a second outlet member 140 that is substantially parallel to the cannula's second nasal insert 130. The second outlet member 140 and second nozzle 130 are also preferably positioned on opposite sides of the base portion 105. Nozzles 125, 130 also may have nozzle outlets 181, 182 respectively.

In various embodiments of the invention, a sensor (e.g., a pressure, temperature, or $O_2$ sensor) is provided in communication or adjacent at least one of (and preferably each of) the cannula's outlets 136, 141 and is used to measure the properties of gas from that outlet 136, 141. In a further embodiment of the invention, accessory tubing is used to connect each outlet 135, 140 with at least one corresponding sensor (and/or at least one external monitoring device) that may, for example, be spaced apart from the cannula 10.

In yet another embodiment of the invention, one or more sensors are provided within the conduit, and used to measure the properties of gas accessed through the conduit. In this embodiment, information from each sensor may be relayed to a control system outside the cannula via, for example, an electrical wire that extends from the sensor and through the outlet 135, 140 of the conduit in which the sensor is disposed.

In alternative embodiments of the invention, each of the cannula's conduits may extend: (1) from the conduit inlets 152, 154; (2) through, or adjacent, a side wall of one of the nozzles 125, 130; (3) through, or adjacent, a side wall of the base portion 105; and (4) to an outlet 135, 140 that is defined within, or disposed adjacent, the base portion 105. In one such embodiment, the conduit comprises a substantially tubular portion that is disposed adjacent an interior surface of the cannula's base portion.

Figure 2:
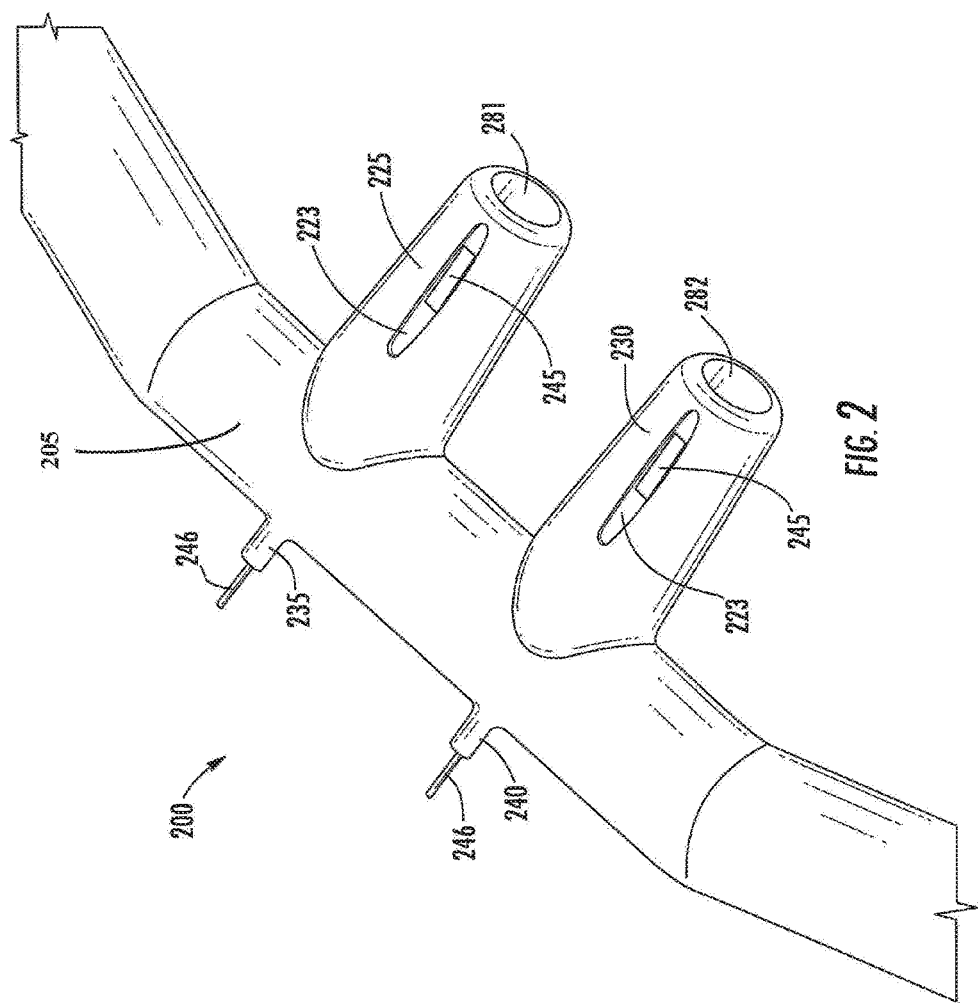
FIG. 2 is a perspective view of a nasal cannula according to a further embodiment of the invention.

As may be understood from FIG. 2, in certain embodiments of the invention, the cannula 200 includes at least one sensor 245 that is integrated into an exterior portion of the cannula 200 (e.g., within a recess 223 formed within an exterior surface of one of the cannula's nozzles, nozzles 225, 230). In this embodiment, information from the sensor 245 may be relayed to a control system outside the cannula 200 via an electrical wire 246 that extends from the sensor 245, through a conduit, and out an outlet 235, 240 in the conduit. In various embodiments of the invention, the conduit extends through or adjacent an interior portion of a sidewall of one of the nozzles 225, 230 and/or through or adjacent an interior portion of a sidewall of the base portion 205. Nozzles 225, 230 also have nozzle outlets 281, 282 respectively.

In particular embodiments of the invention, at least one sensor 245 is fixedly attached to the cannula 10 so that it may not be easily removed by a user. Also, in particular embodiments, at least one sensor 245 is detachably connected adjacent the cannula 10 so that the sensor 245 may be easily detached from (and, in certain embodiments, reattached to) the cannula 10.

The cannula 1000 includes a base portion 1005, which is hollow, elongated, and tubular, that includes a central portion 1010, a first end portion 1015, and a second end portion 1020. The first and second end portions 1015 and 1020 may be angled relative to the central portion 1010, as shown in FIG. 10. In various embodiments of the invention, the cannula 1000 includes a first tubing inlet 1017 adjacent the outer end of the first end portion 1015, and a second tubing inlet 1022 adjacent the outer end of the second end portion 1020.

The cannula 1000 further comprises a pair of hollow, elongated, tubular nozzles (a first nozzle 1026 and a second nozzle 1031) that extend outwardly from the base portion 1005. In various embodiments, the respective central axes of the nozzles 1026, 1031 are substantially parallel to each other and are substantially perpendicular to the central axis of the central portion 1010 of the base portion 1005. In various embodiments, the nozzles 1026, 1031 define passageways that are in gaseous communication with the interior of the base portion 1005. In particular embodiments of the invention, the first and second nozzles 1026, 1031 are adapted to be positioned outside of a user's nares while the cannula is in use. In particular embodiments, the nozzles 1026, 1031 each define a respective nozzle outlet. For example, the first nozzle 1026 defines a first nozzle outlet 1083, and the second nozzle 1031 defines a second nozzle outlet 1084. In various embodiments, when the cannula 1000 is operatively positioned adjacent a user's nares, each of the nozzle's outlets 1083, 1084 is positioned to direct a focused flow of gas into a corresponding one of the user's nares.

Figure 12:
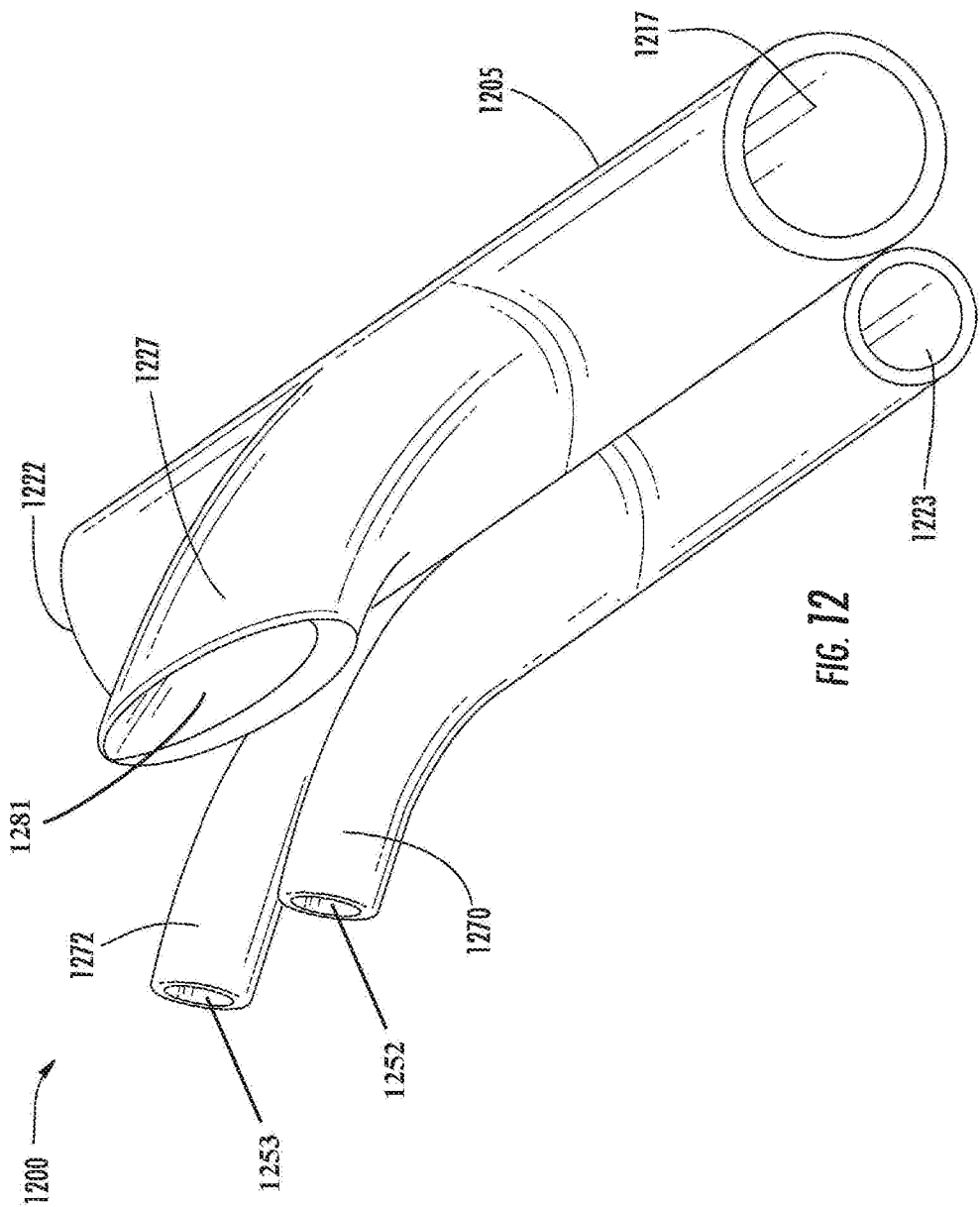
FIG. 12 is a perspective view of a nasal cannula according to yet another embodiment of the invention.

In alternative embodiments, such as the embodiment shown in FIG. 12, the cannula 1200 may include a single nozzle 1227 that defines a passageway that is in gaseous communication with an interior portion of the base portion 1205. As described in greater detail below, in various embodiments, the nozzle 1227 extends outwardly from the base portion 1205 and has an oblong, or elliptical, cross-section. In this and other embodiments, the nozzle 1227 is shaped to deliver a focused flow of gas simultaneously into both of a user's nares when the cannula 1200 is in use.

In various embodiments, the nasal cannula includes one or more elongate extensions that are adapted for insertion into one or more of the user's nares. For example, returning to the embodiment shown in FIG. 10, the cannula 1000 may include multiple elongate extensions (for example a first elongate extension 1070 and a second elongate extension 1072) that are long enough to allow each of the elongate extensions 1070, 1702 to be inserted into a respective one of the user's nares while the cannula 1000 is in use. In embodiments, elongate extensions 1070, 1072 may have conduit inlets 1052, 1053 respectively. In various embodiments, each of the elongate extensions 1070, 1072 may have a central axis that runs substantially parallel to the central axis of a corresponding nozzle 1026, 1031. For example, as can be understood from FIG. 10, in certain embodiments, a first elongate extension 1070 has a central axis that lies substantially parallel to and below the central axis of a corresponding first nozzle 1026, when the cannula is operatively positioned adjacent a user's nares. Similarly, in various embodiments, a second elongate extension 1072 has a central axis that lies substantially parallel to and below the central axis of a corresponding second nozzle 1031, when the cannula 1000 is operatively positioned adjacent a user's nares. In various other embodiments, the elongate extensions may lie within, and extend outwardly from, their corresponding nozzles 1070, 1072.

As a further example, FIG. 12 illustrates an exemplary cannula 1200 having multiple elongate extensions (a first elongate extension 1270 and a second elongate extension 1272), which both lie substantially beyond a single nozzle 1227 when the cannula 1200 is in an operative position adjacent the user's nose. In some embodiments, the central axes of the first and second elongate extensions 1270, 1272, may be substantially parallel to the central axis of the nozzle 1227. Also, in various embodiments, one or both of the elongate extensions 1270, 1272 may lie within the nozzle 1227. In this and other embodiments, a distal end of each of the elongate extensions 1270, 1272 may extend beyond a distal end of the nozzle 1227. Elongate extensions 1270, 1272 may have conduit inlets 1252, 1253 respectively, while nozzle 1227 has a nozzle outlet 1281.

As described above, in certain embodiments of the invention, the nasal cannula includes one or more sensors that are adapted to measure gas data (e.g., gas pressure) within the user's nares while the cannula is in use. For example, the cannula 1000 shown in FIG. 10 may include a sensor positioned adjacent the distal end of one or both of the first and second elongate extensions 1070, 1072. In various embodiments, each elongate extension may be adapted to: (1) support a sensor adjacent (e.g., at) the distal end of the elongate extension; and (2) support a wire that is simultaneously connected to the sensor and a control mechanism that is adapted to adjust the properties of gas flowing through the cannula 1000.

In other embodiments, the elongate extensions define conduits. For example, one or more sensor(s) may be positioned within the interior or exterior of the elongate extensions and information from the sensor(s) may be relayed to a control system via a wire extending through a conduit (for example, elongate extension conduit 1023 of FIG. 10) or passages defined by each of the elongate extensions. In one embodiment, as shown, for example, in FIG. 10, the elongate extension conduit 1023 is shaped similarly to the base portion 1005, and lies substantially below the base portion 1005 when the cannula 1000 is operatively in use. In various embodiments, the elongate extension conduit 1023 is positioned within the base portion 1005 such that the first and second elongate extensions 1070, 1072 lie within, and extend outwardly from, the respective first and second nozzles 1026, 1031.

In various embodiments, each elongate extension defines a respective sensing conduit. For example, in certain embodiments, each sensing conduit is adapted to provide a passage that permits sensing or gaseous communication between a user's nares and a control system or other device for measuring and adjusting the properties of the air. In this and other embodiments, a sensor may be positioned at the control box to measure the properties (e.g., pressure) of air in the user's nares. In some embodiments, the elongate extensions define a conduit that serves both as an air passageway as well as a conduit for allowing a wire to pass from a sensor positioned adjacent the distal tip of the elongate extension to the control system or other device.

Data Monitored by Sensors

In various embodiments of the invention, such as those described above, one or more sensors may be positioned to measure gas data within an interior portion of one of the nasal cannula's conduits, or to measure gas data adjacent an exterior portion of the cannula. In such embodiments, one or more sensors may be, for example, positioned adjacent an interior or exterior surface of the cannula. In certain embodiments of the invention, one or more of the cannula's sensors is adapted to monitor one or more of the following types of data within the cannula's conduits, or adjacent the cannula's exterior surface (e.g., adjacent a side portion, or distal end of, one of the cannula's nozzles): (1) gas pressure; (2) gas flow rate; (3) carbon dioxide content; (4) temperature; (5) level; and/or (6) oxygen content.

Absolute Vs. Relative Pressure Measurements

In various embodiments of the invention, the cannula may be configured for sensing absolute pressure within, or adjacent, a particular portion of the cannula. Similarly, in particular embodiments, the cannula may be configured to measure the difference between the pressures at two different locations within the cannula. This may be done, for example, by providing two separate sensors (e.g., that are positioned in different locations within one of the cannula's conduits), or by providing two physically distinct gas intake conduits, each of which is adapted for routing gas from a different location within the cannula. For example, in various embodiments of the invention shown in FIG. 1, the first conduit inlet 152 may be connected to a first conduit that is adapted for routing gas to a first sensor, and the second conduit inlet 154 may be connected to a physically separate second conduit that is adapted for routing gas to a second pressure sensor. Information from the first and second sensors may then be used to calculate the difference in pressure between the first and second inlets 152, 154. Alternatively, a differential pressure sensor may be used.

Suitable Sensors

Suitable sensors for use with various embodiments of the invention include electronic and optical sensors. For example, suitable sensors may include: (1) Disposable MEM Piezoelectric sensors (e.g., from Silex Microsensors); (2) light-based sensors such as a McCaul $O_2$ sensor—see U.S. Pat. No. 6,150,661 to McCaul; and (3) Micro-pressure sensors, such as those currently available from Honeywell.

Non-Sealing Feature

Figure 4:
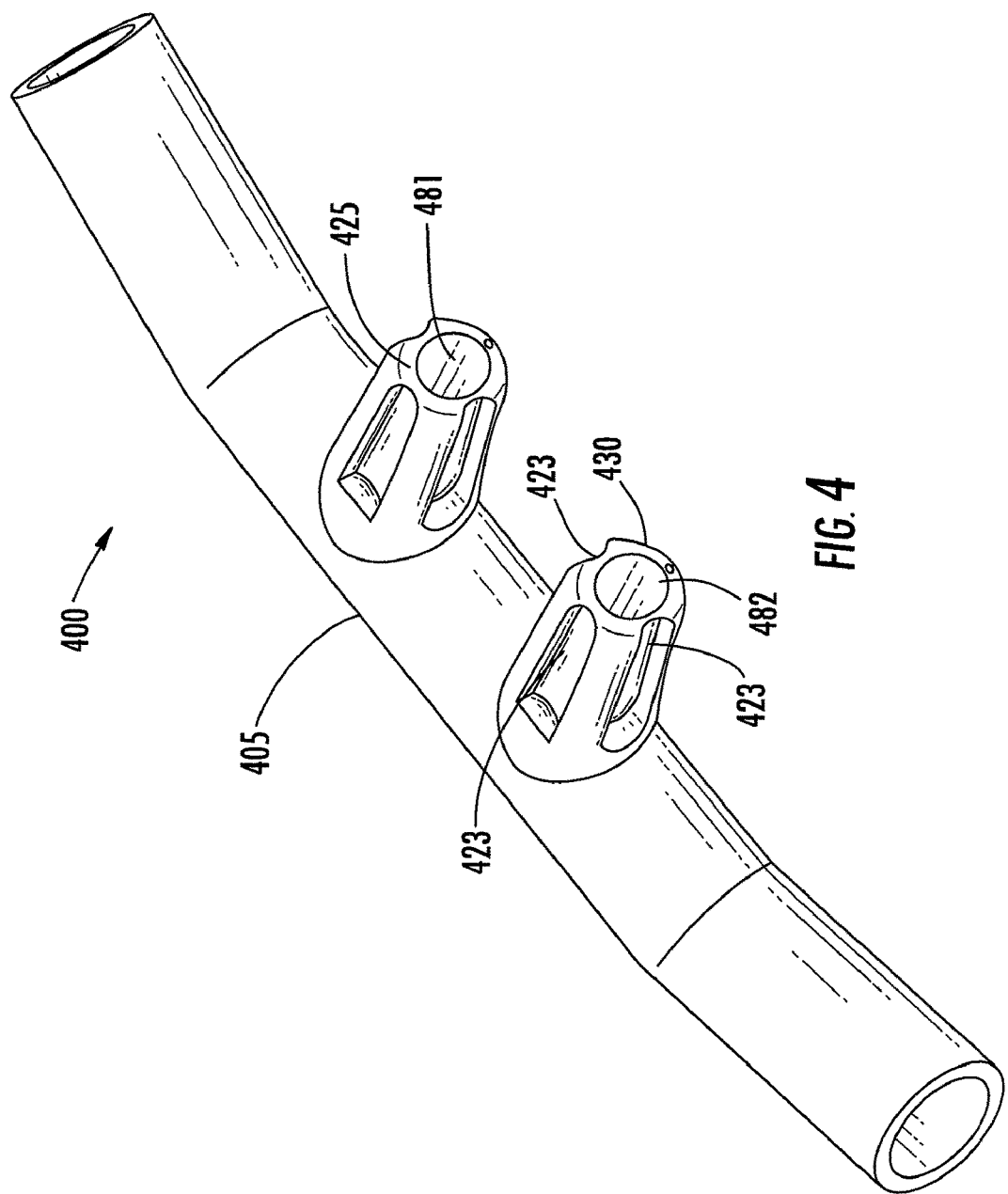
FIG. 4 is a perspective view of a nasal cannula according to yet another embodiment of the invention.

As shown in FIG. 4, in various embodiments of the invention, cannula 400 has one or more nozzles 425, 430 that includes one or more recesses 423 (e.g., grooves, semicircular recesses, or other indentations or conduits) that extend along a length of the nozzle's exterior surface. As may be understood from this figure, in various embodiments of the invention, at least one of these recesses 423 is an elongate groove that extends from adjacent a distal surface of the nozzle 425, 430 and past the midpoint between: (1) the nozzle's distal tip and (2) the portion of the nozzle 425, 430 that is immediately adjacent the nasal cannula's base portion 405. As may also be understood from this figure, in various embodiments of the invention, each groove 423 extends substantially parallel to the central axis of its respective nozzle 425, 430.

Figure 3:
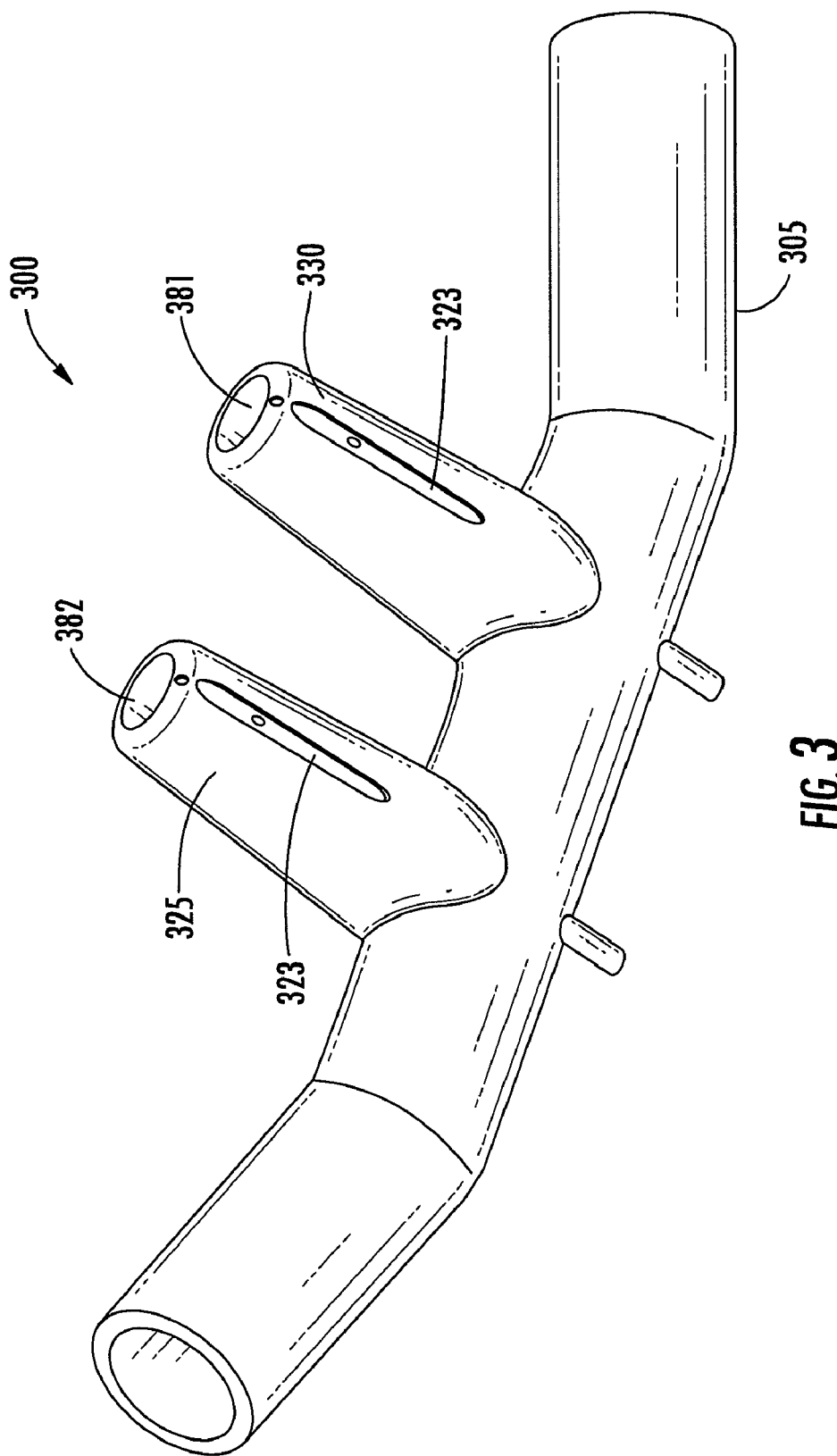
FIG. 3 is a perspective view of a nasal cannula according to another embodiment of the invention.

Nozzles 425, 430 also have nozzle outlets 481, 482 respectively. As shown in FIG. 3, in various embodiments of the invention, cannula 300 has one or more nozzles 325, 330 that includes one or more recesses 323 that extend along a portion of length of the nozzle's exterior surface. As may be understood from this figure, in various embodiments of the invention, at least one of these recesses 323 is an elongate groove that extends from adjacent a distal surface of the nozzle 325, 330 between: (1) the nozzle's distal tip and (2) the portion of the nozzle 325, 330 that is immediately adjacent the nasal cannula's base portion 305. As may also be understood from this figure, in various embodiments of the invention, each groove 323 extends substantially parallel to the central axis of its respective nozzle 325, 330. Nozzles 325, 330 also have nozzle outlets 381, 382 respectively.

In particular embodiments of the invention, such as the embodiment shown in FIG. 4, at least one of the nasal cannula's nozzles 425, 430 is configured so that when the nozzles 425, 430 are operatively positioned within a user's nares, the nozzles do not form an airtight seal with the user's nares. This may be due, for example, to the ability of air to flow adjacent the user's nare through recesses 423 in the nozzles 425, 430 when the user is wearing the nasal cannula.

Figure 5:
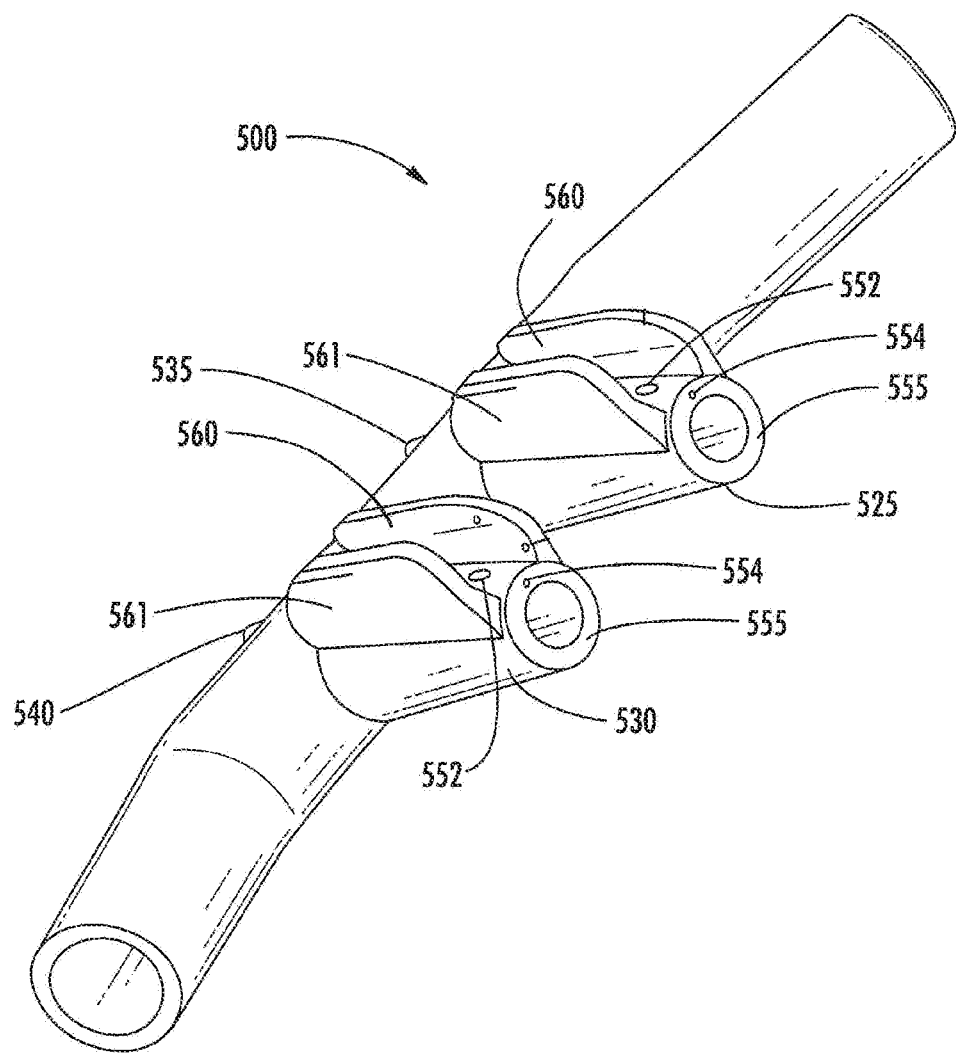
FIG. 5 is a front perspective view of a nasal cannula according to a further embodiment of the invention.

FIGS. 5-8 depict additional embodiments of the invention that are configured so that when the cannula's nasal inserts are operatively positioned adjacent (e.g., partially within) the user's nares, the nasal inserts do not form a seal with the user's nares. For example, in the embodiment shown in FIG. 5, illustrating cannula 500, at least one (and preferably both) of the cannula's nasal inserts, nozzles 525, 530, comprise a nozzle body portion 555 (which may, for example, be substantially tubular), and one or more flange portions 560, 561 that are adapted to maintain a physical separation between an exterior side surface of the nozzle body portion 555 and a user's nare when the nozzle 525, 530 is inserted into the user's nare.

For example, in the embodiment of the invention shown in FIG. 5, each of the nozzles 525, 530 includes nozzle body portion 555 and a pair of co-facing, elongated flanges, flanges 560, 561, that each have a substantially C-shaped cross section. In this embodiment, these flanges 560, 561 cooperate with a portion of the exterior of the nozzle body portion 555 to form a substantially U-shaped channel (which is one example of a "nasal lumen") through which ambient air may flow to and/or from a user's nasal passages when the cannula 500 is operatively in place within the user's nares. In this embodiment, when the nozzles 525, 530 are properly in place within the user's nares, respiratory gas is free to flow into the -user's nose through the nozzle body portion 555, and ambient air is free to flow into and out of the user's nose through a passage defined by: (1) the flanges 560, 561; (2) the exterior side surface of the nozzle body portion 555 that extends between the flanges 560, 561; and (3) an interior portion of the user's nose. In various embodiments, air may flow to and/or from a user's nose through this passage when the cannula 500 is operatively in place within the user's nares. A pathway (e.g., a semicircular pathway) may be provided adjacent the interior end of this U-shaped channel, which may act as a passageway for gas exhaled and inhaled through the U-shaped channel. In embodiments, nozzles 525, 530 may have conduit inlets 552, 554, and cannula 500 may have conduit outlets 535, 540.

Figure 6:
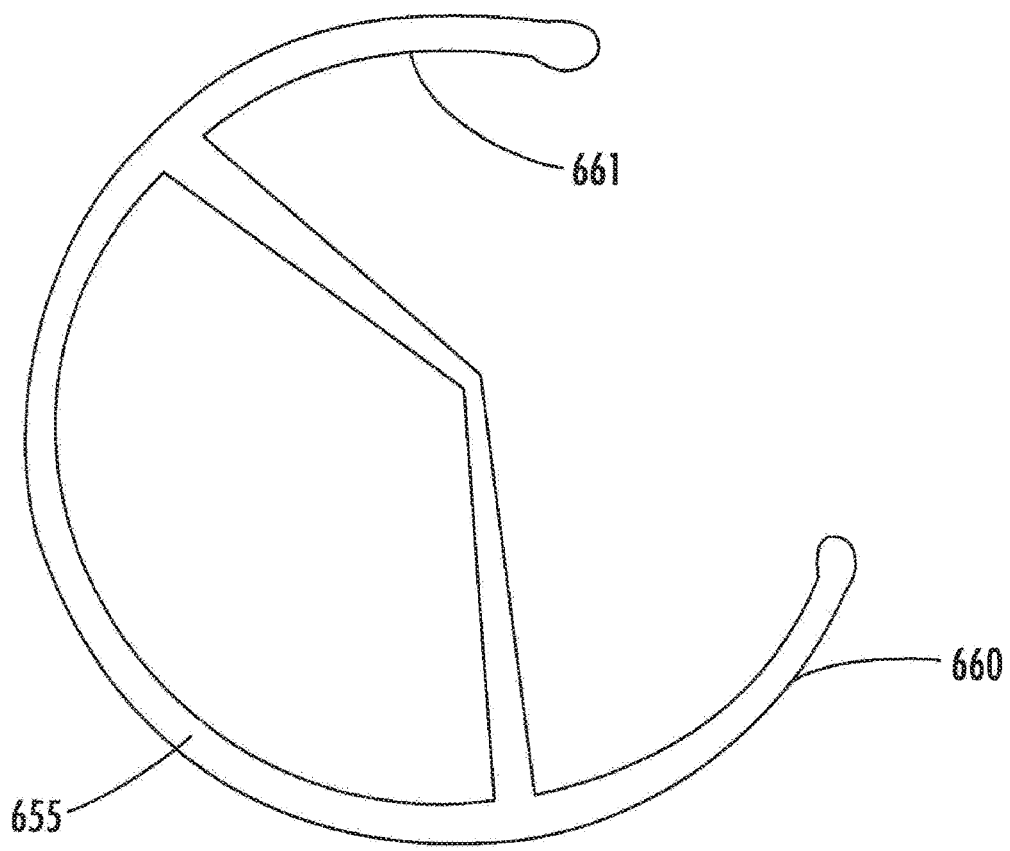
FIG. 6 depicts a cross section of a nasal insert of a nasal cannula according to a particular embodiment of the invention.

The general embodiment shown in FIG. 5 may have many different structural configurations. For example, as shown in FIG. 6, which depicts a cross section of a nozzle according to a particular embodiment of the invention, the respiratory gas passageways of the nozzles 655 of a cannula may be in the form of a tube having an irregular cross section (e.g., a substantially pie-piece-shaped cross section) rather than a circular cross section. Alternatively, as may be understood from FIG. 7, the respiratory gas passageways of the nozzles 755 of a cannula may be in the form of a tube having a substantially half-circular cross section rather than a circular cross section.

Figure 7:
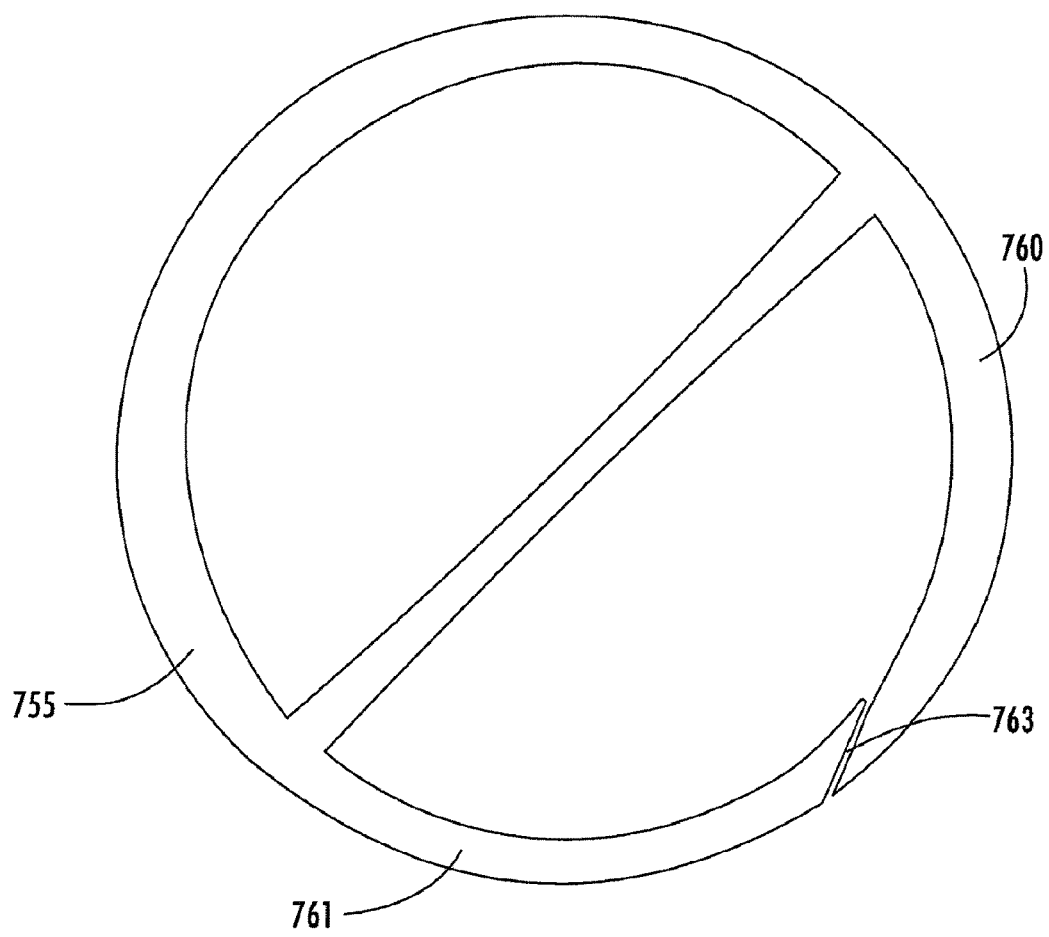
FIG. 7 depicts a cross section of a nasal insert of a nasal cannula according to a further embodiment of the invention.

Similarly, as may be understood from FIGS. 6 and 7, the shape and size of the cannula's flanges may vary from embodiment to embodiment. For example, in the embodiment shown in FIG. 6, each of the flanges 660, 661 has a relatively short, substantially C-shaped cross section and the distal ends of flanges 660, 661 are spaced apart from each other to form a gap. As shown in FIG. 7, in other embodiments, each of the flanges 760, 761 may have a relatively long, substantially C-shaped cross section and the distal ends of the flanges 760, 761 may be positioned immediately adjacent each other.

As may be understood from FIG. 7, in various embodiments of the invention, a separation 763 (e.g., a slit, such as an angular slit) is provided between the flanges 760, 761. This may allow the flanges 760, 761 to move relative to each other and to thereby conform to the nare in which the nozzle is inserted. In other embodiments, the cross section of the nozzles is substantially as that shown in FIG. 7, except that no separation 763 is provided within the semi-circular flange portion. Accordingly, in this embodiment of the invention, a substantially semi-circular portion of the exterior of the air passageway cooperates with a substantially semi-circular portion of the flange portion to form an exterior having a contiguous, substantially circular cross section. One such embodiment is shown in FIGS. 8A-8C.

As may be understood from FIGS. 8A-8C, in this embodiment, when the cannula 800 is in use, respiratory gas may flow into the user's nose through inspiratory passageways 881 that extend through each of the nozzles 825, 830. Inspiratory passageways 881 are in gaseous communication with the interior of base portion 805 as shown in FIG. 8C. An expiratory passageway 885 of substantially semi-circular cross section extends between the distal end of each nozzle 825, 830 to a substantially semicircular expiratory passageway outlet 865 defined within the cannula's base portion 805. In various embodiments, when the cannula 800 is in use, the user may exhale or both inhale and exhale gas through this expiratory passageway 885. As previously mentioned, this cannula embodiment does not form a seal within the user's nares due to the expiratory passageways 885, even if the nozzles 825, 830 tightly fit within the nares. In further embodiments, nozzles 825, 830 may have recesses 823.

In certain embodiments, as discussed above, a conduit 850 is provided in each of the nozzles 825, 830 (see FIG. 8C) and may have conduit inlets 852, 854. Each of these conduits 850 may be adapted to facilitate measuring gas data by: (1) receiving gas from the interior of a corresponding expiratory passageway 885 and/or from adjacent the exterior of one of the nozzles 825, 830, and/or (2) guiding the gas out of a corresponding conduit outlet 835, 840 in the cannula 800. As discussed above, one or more sensors may be disposed within, or adjacent, the conduit 850 and used to assess one or more attributes of gas flowing through or adjacent the conduit 850.

It should be understood that the embodiments of the invention shown in FIGS. 4-8 and related embodiments may have utility with or without the use of sensors or sensor conduits. It should also be understood that the various nozzles may be configured to be disposed in any appropriate orientation within the user's nares when the cannula is operably positioned within the user's nares. For example, in one embodiment of the invention, the cannula may be positioned so that the cannula's nasal lumen is immediately adjacent, or so that it faces anterior-laterally away from, the user's nasal spine.

Figure 9:
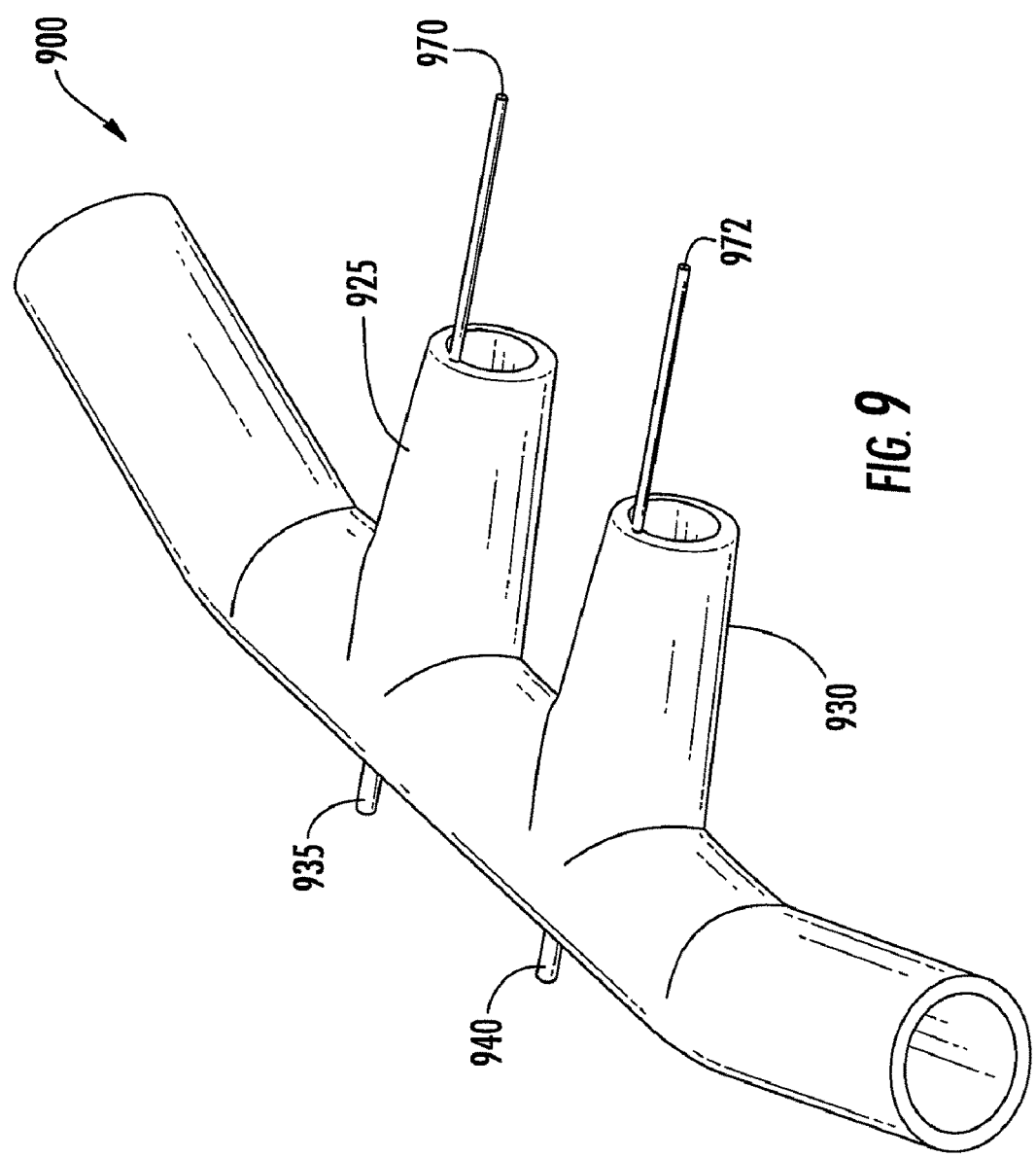
FIG. 9 is a perspective view of a nasal cannula according to a further embodiment of the invention.

Turning to yet another embodiment of the invention, as shown in FIG. 9, the cannula 900 may be adapted so that a conduit inlet 970, 972 for at least one sensor (or the sensing conduit itself) is maintained adjacent, and spaced a predetermined distance apart from, the distal end of a respective nozzle 925, 930. In this embodiment, the sensor (or conduit inlet) may be spaced apart from the rest of the cannula 900 adjacent one of the nozzle outlet openings. In embodiments, cannula 900 may have conduit outlets 935, 940.

As may be understood from FIG. 10, in various embodiments, the first and second nozzles 1026, 1031 of the nasal cannula are configured to remain outside of the user's nares while the cannula is in use. For example, the nozzles may be of a length such that, when the cannula is in use, the distal ends of the nozzles 1026, 1031 lie adjacent, but outside, the user's nares. By preventing insertion of the nozzles 1026, 1031 into the nares, sealing of the nares can be avoided. As may be understood from FIG. 13, in various embodiments, when the nasal cannula is in an operative position adjacent the user's nares, an outlet portion (and distal end) of each nozzle 1326, 1331 is spaced apart from, and substantially in-line (e.g., substantially co-axial) with, a corresponding one of the patient's nares. In various embodiments, when the nasal cannula is operatively in use, the outlet of each nozzle is spaced apart from the patient's nares and each nozzle is positioned to direct a focused flow of gas into a particular respective one of the user's nares.

Referring to FIG. 11, cannula 1100 includes a base portion 1105, which is hollow, elongated, and tubular, that includes a central portion 1110, a first end portion 1115, and a second end portion 1120. The first and second end portions 1115, 1120 may be angled relative to the central portion 1110, as shown in FIG. 11. In various embodiments of the invention, the cannula 1100 includes a first tubing inlet 1117 adjacent the outer end of the first end portion 1115, and a second tubing inlet 1122 adjacent the outer end of the second end portion 1020. As may be understood from FIG. 11, in particular embodiments, a stop 1190 may extend outwardly from the base portion 1105 of the cannula 1100. In some embodiments, the stop 1190 lies in between the first and second nozzles 1126, 1131 and defines a central axis that runs substantially parallel to the respective central axes of the nozzles 1126, 1131. The stop 1190, in some embodiments, may extend outwardly from the base portion 1105 a length greater than that of the nozzles 1126, 1131. In this manner, the stop 1190 prevents the nozzles 1126, 1131 from being inserted into the user's nares when the cannula 1100 is in use.

For example, the stop 1190 may be positioned so that when the cannula 1100 is in use, the stop is designed to engage the columella of the user's nose and thereby prevent the nozzles 1126, 1131 from being inserted into the user's nares. In various embodiments, the first and second nozzles 1126, 1131 are positioned on either side of the stop 1190 so that when the cannula 1100 is operatively in use, the each nozzle 1126, 1131 will be spaced apart from a respective particular one of the patient's nares and will be positioned to direct a focused flow of gas into that particular nare by, for example, being positioned so that the outlet (and distal end) of each nozzle (first nozzle outlet 1183 and second nozzle outlet 1184) is substantially in-line (e.g., substantially co-axial) with, a corresponding one of the patient's nares. Similar to cannula 1000, cannula 1100 has elongate extensions 1170, 1172 that have conduit inlets at the distal ends. Elongate extensions 1170, 1172 are in gaseous communication with conduits, such as conduit 1123.

As may be understood from FIG. 12, in various embodiments, the cannula 1200 may include only a single nozzle 1227. The nozzle 1227, in various embodiments, has an oblong or substantially elliptical cross-section. In these embodiments, the major axis of the ellipse runs substantially parallel to the central axis of the base portion 1205 of the nasal cannula. In one embodiment, the nozzle 1227 is wide enough to allow air to flow into both of a user's nares when the nasal cannula is in use. For example, in various embodiments, the width of the nozzle 1227 (e.g., a length defined by the major axis of the nozzle's elliptical cross section) may be approximately equal to (or greater than) the total width of the user's nares. In various embodiments, the cannula 1200 includes a first tubing inlet 1217 and a second tubing inlet 1222.

Figure 14:
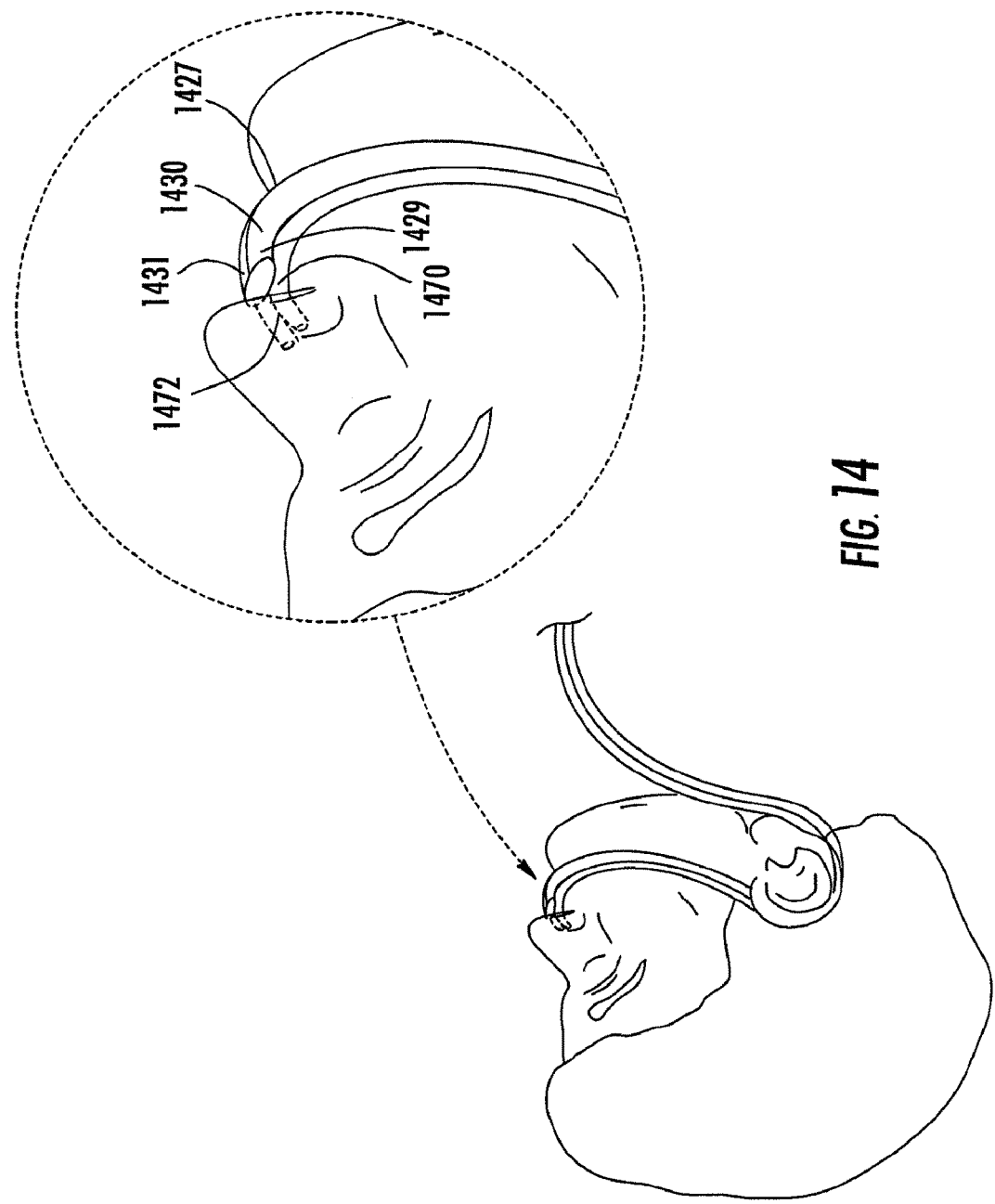
FIG. 14 illustrates another embodiment of a nasal cannula in use on a patient, according to a further embodiment of the invention.

As may be understood from FIG. 14, when the nasal cannula is operatively in use, a first lateral side 1430 of the nozzle 1429 is spaced apart from, and adjacent, a user's first nare, and a second lateral side 1431 of the nozzle 1429 is spaced apart from, and adjacent, the user's second nare. In this and other configurations, the nozzle 1429 is configured to direct a focused flow of gas simultaneously into each of the user's nares. In various embodiments, when the nozzle is of a certain width, for example, approximately equal to (or greater than) the total width of the user's nares, and other widths, the nozzle 1429 is sufficiently wide to prevent the nozzle 1429 from being inserted into a user's nare, thus preventing sealing of the nasal cannula with the nare and/or is sufficiently wide to act as a stopping feature to prevent the nozzle 1429 from being inserted in the user's nares when the nasal cannula is in use. In various embodiments, first and second elongate extensions 1470, 1472 are inserted into the patient's nares. In various embodiments, the cannula has tubing 1427 which may have multiple conduits and may be positionable around the ear(s) of the user during use.

In various other embodiments, the cannula's single nozzle may have a different cross-section that is not oblong or elliptical. For example, the nozzle may have a substantially circular cross-section, with a diameter that is wide enough to allow air to flow into both of a user's nares when the cannula is in use, while simultaneously being wide enough to prevent insertion into a single nare. In various other embodiments, the nasal cannula may have more than one nozzle, each having a substantially oblong cross section and a width that prevents insertion into each of a user's nares.

In various embodiments, one or more of the cannula's elongate extensions has a diameter that is adapted to prevent sealing with the user's nares. For example, the elongate extension(s) may have a diameter that is substantially narrower than a user's nares, so that sealing is avoided. In other embodiments, the elongate extension(s) may include features such as grooves or recesses, as described above, to prevent sealing when inserted into a user's nare(s).

Exemplary Use of the Cannula

To use a cannula according to a particular embodiment of the invention, a physician or technician may have a patient use the cannula for a brief period of time, while the physician or technician monitors information received from the cannula's various sensors, or the information may be recorded for later analysis. The physician or technician may then use this information to adjust the structure or operation of the cannula until the cannula's sensors indicate that the patient's upper airway environment satisfies certain conditions.

Similarly, in various embodiments, the cannula's sensors may be used to monitor conditions within the patient's upper airway over time. In a particular embodiment, the cannula's sensors may be connected to a control system that will automatically alter or modify the flow of therapeutic gas into the cannula if information from the sensor indicates undesirable conditions within the patient's upper airway. In further embodiments of the invention, the sensor is connected to a control system that issues an alarm if information from the cannula's sensors indicates undesirable conditions within the patient's airway.

Figure 13:
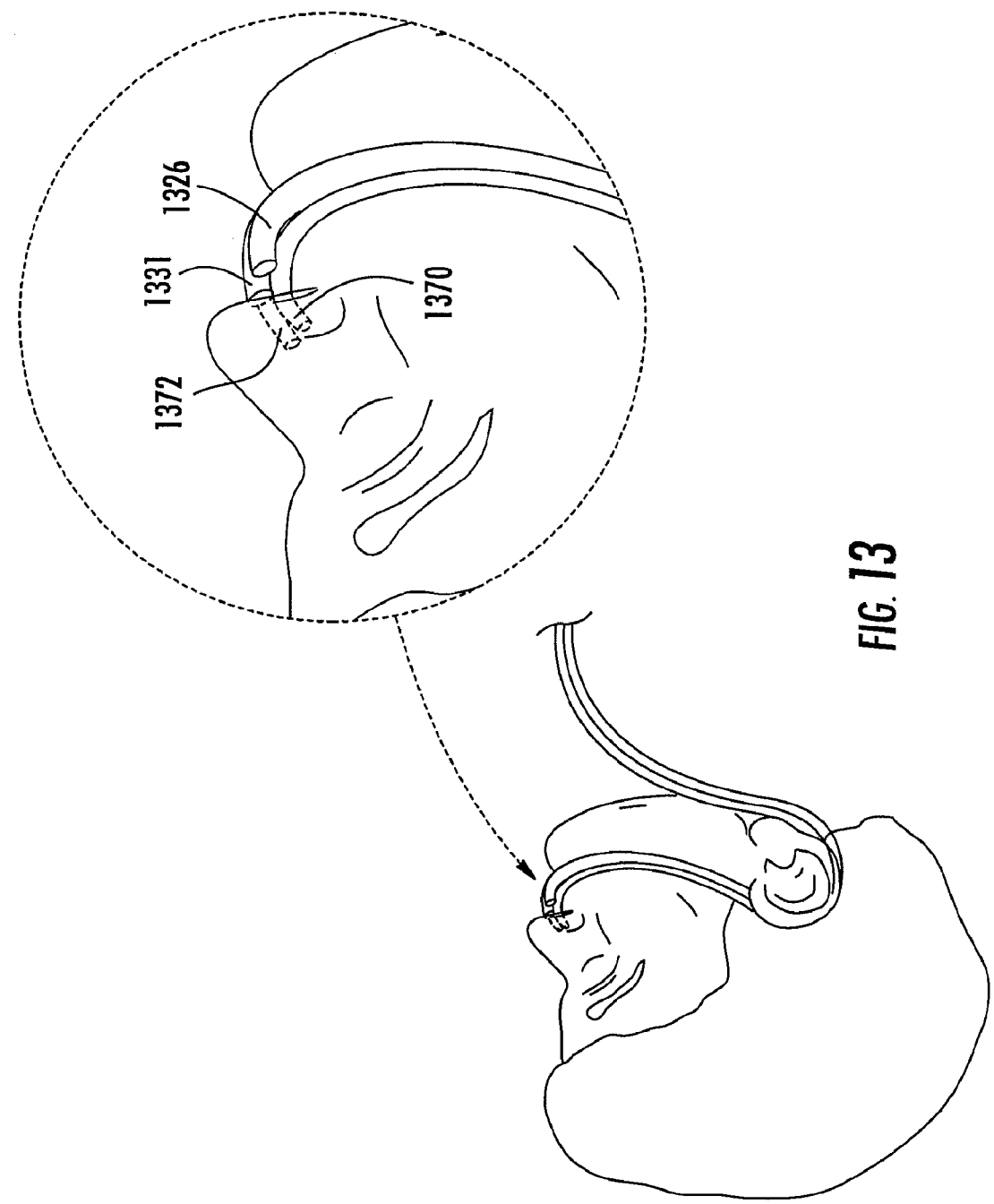
FIG. 13 illustrates an embodiment of a nasal cannula in use on a patient, according to one embodiment of the invention.

FIGS. 13 and 14 depict various embodiments of nasal cannulas being used on a patient. As may be understood from FIG. 13, for example, a nasal cannula is used on a young or small infant for high flow therapy. For example, a nasal cannula similar to that shown in FIG. 10 can be used. In various embodiments, first and second elongate extensions 1370, 1372 are inserted into the patient's nares, while corresponding first and second nozzles 1326, 1331 remain adjacent and external to the patient's nares. As may be appreciated, when the nasal cannula is in use, air flows into the patient's nares via the nozzles. FIG. 14 depicts one embodiment of a nasal cannula in use on a patient. In one embodiment, a nasal cannula such as that shown in FIG. 12 can be used. As may be understood from FIG. 14, a nasal cannula having a single nozzle 1429 can be used, in which the nozzle is sized and shaped (e.g., is elliptical and/or wider than a patient's nare) to prevent insertion into the patient's nares. In various other embodiments, nasal cannula having nasal insert type nozzles, as described throughout, can be used. In these embodiments, the nasal inserts are inserted into the user's nares while the cannula is in use. Nasal cannula according to embodiments of the invention can be used on a variety of patients.

High Flow Therapy Device

Figure 17:
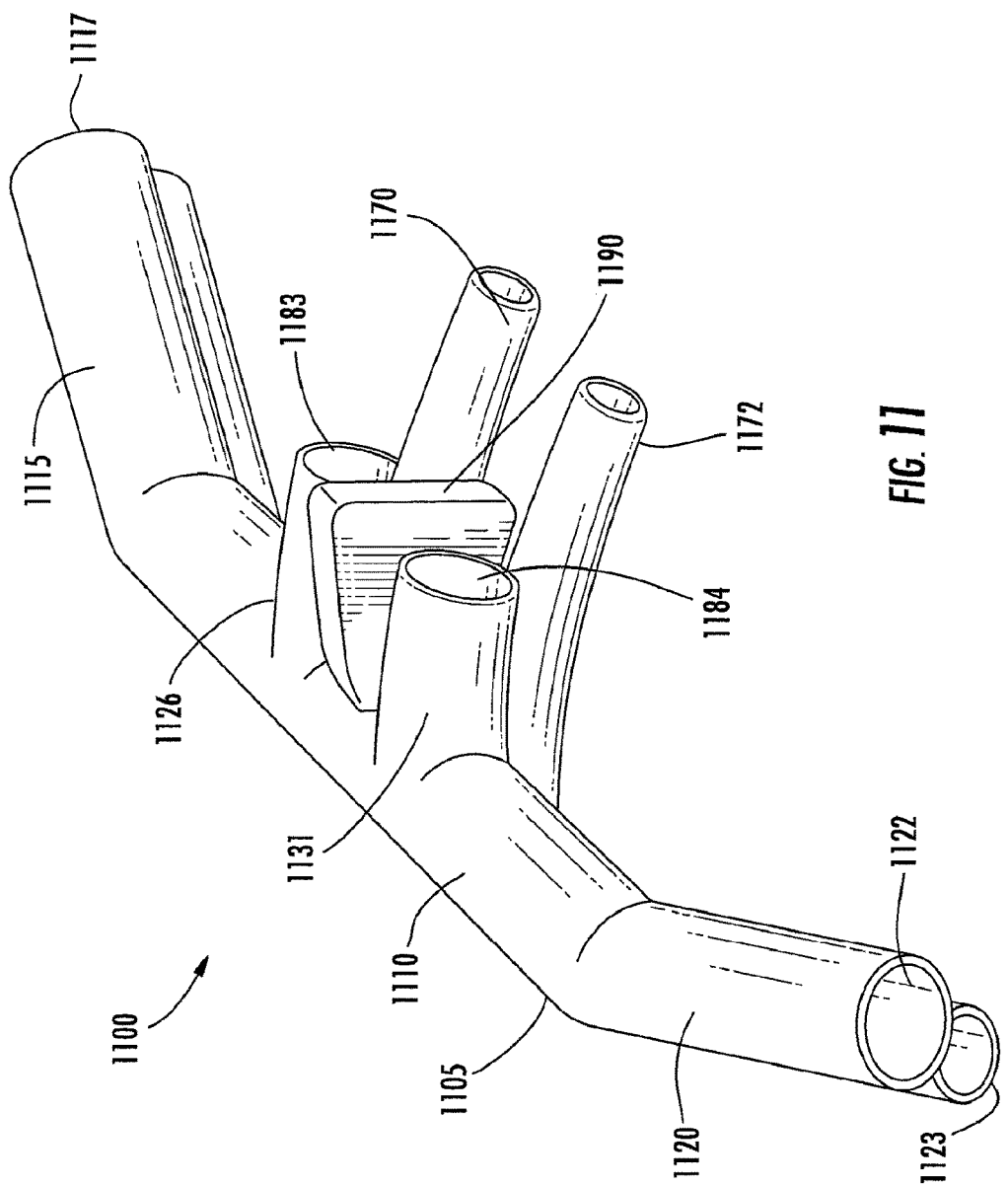
FIG. 17 illustrates a schematic view of the high flow therapy device of FIGS. 15 and 16 with a nasal interface and a patient in accordance with an embodiment of the present disclosure.
Figure 15:
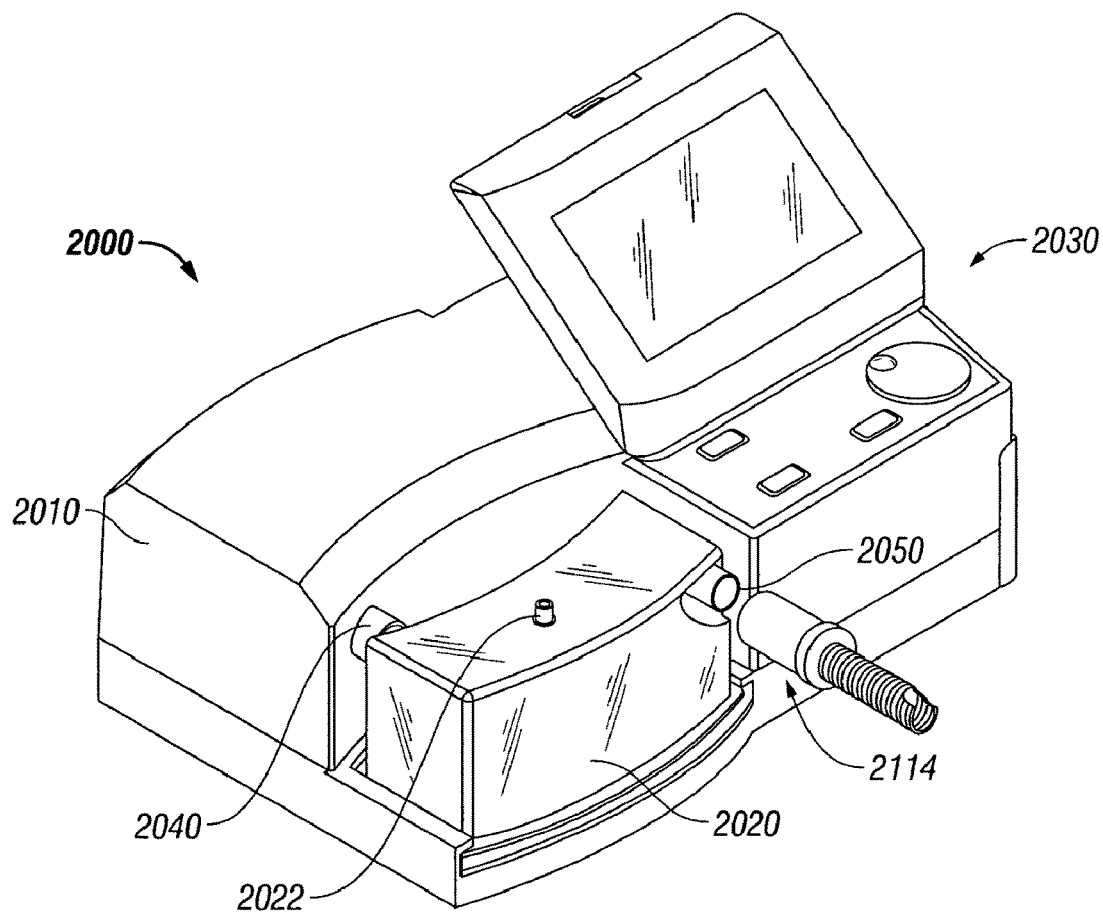
FIG. 15 illustrates a perspective view of a high flow therapy device in accordance with an embodiment of the present disclosure.
Figure 16:
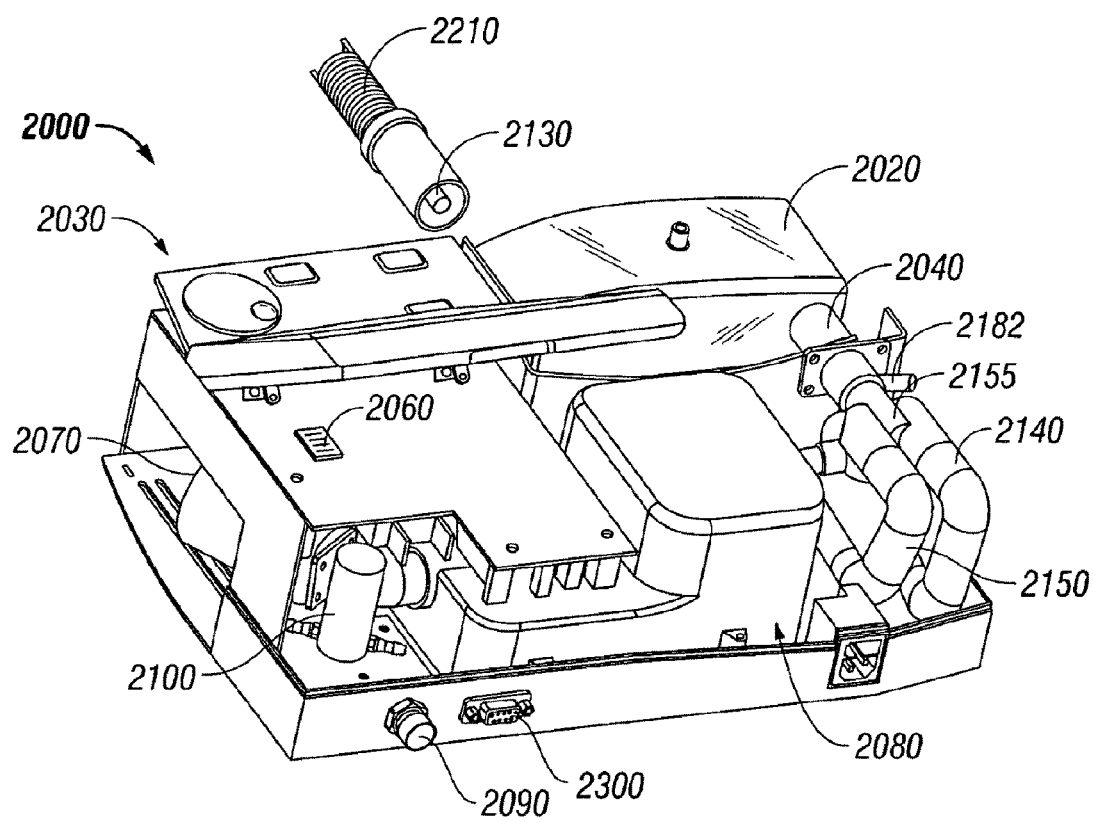
FIG. 16 illustrates a perspective view of the high flow therapy device of FIG. 15 showing internal components, in accordance with an embodiment of the present disclosure.
Figure 17:
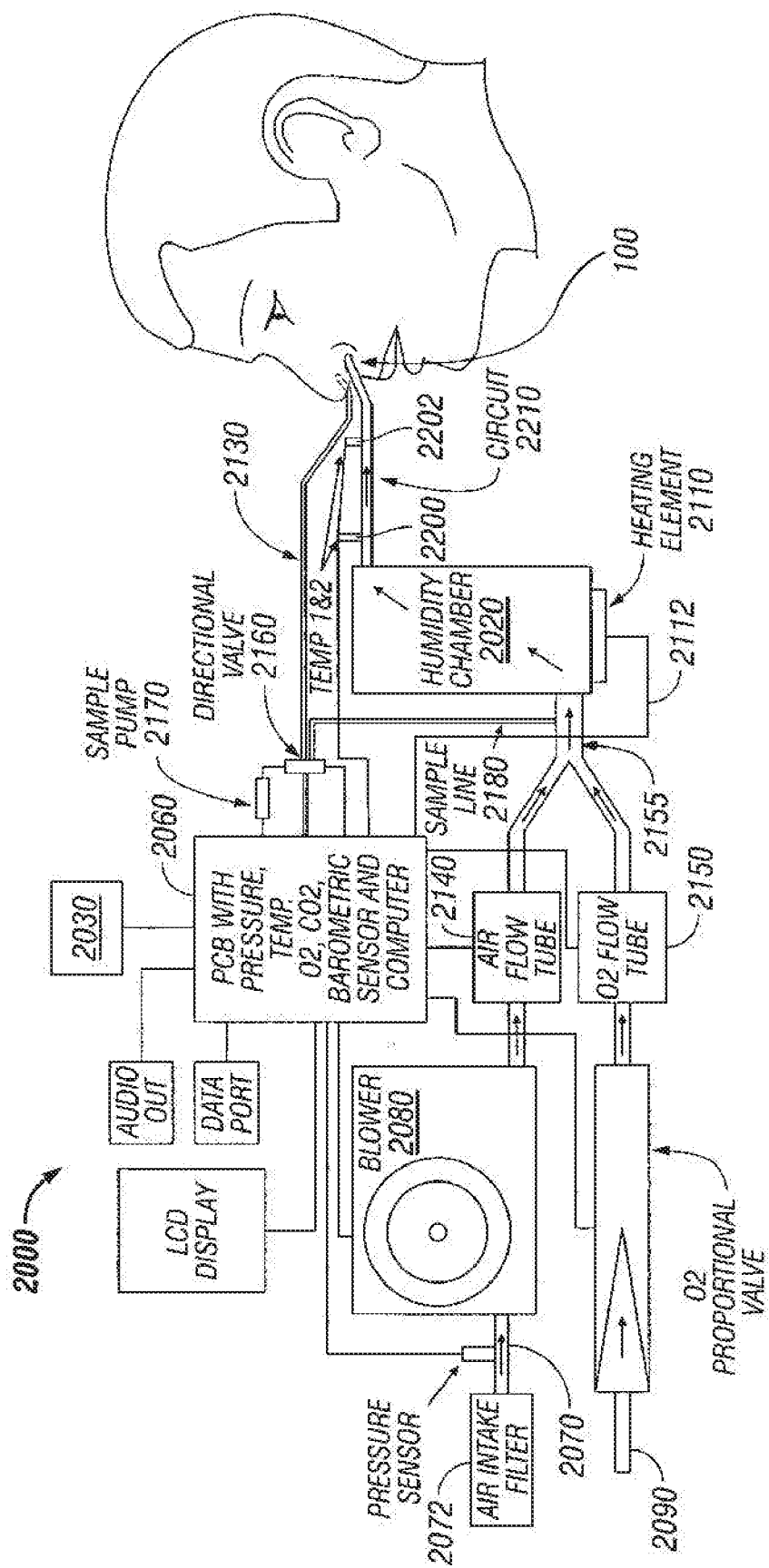

Now referring to FIGS. 15-17, a high flow therapy device 2000 is shown. High flow therapy device 2000 is configured for use with a non-sealing respiratory interface, such as cannula 10, for example, to deliver gas to a patient. In various embodiments, high flow therapy device 2000 is able to heat, humidify, and/or oxygenate a gas prior to delivering the gas to a patient. Additionally, embodiments of high flow therapy device 2000 are able to control and/or adjust the temperature of the gas, the humidity of the gas, the amount of oxygen in the gas, the flow rate of the gas and/or the volume of the gas delivered to the patient.

High flow therapy device 2000 is shown in FIG. 15 including a housing 2010, a humidity chamber 2020 (e.g., vapor generator), a user interface 2030, a gas inlet port 2040 and a gas outlet port 2050. A microprocessor 2060, an air inlet port 2070, a blower 2080, an oxygen inlet 2090 and a proportion valve 2100 are illustrated in FIG. 16. A non-sealing respiratory interface (such as a cannula illustrated in FIGS. 1-14 (e.g., 10 or 1200), hereinafter referred to as 100, is configured to mechanically cooperate with gas outlet port 2050 to supply a patient with gas. The user interface 2030 includes a user display that is adapted to display data as a graph. The data can include, but is not limited to, pressure, amount of oxygen in the gas, the flow rate of the gas and/or the volume of the gas delivered to the patient. As illustrated in FIG. 15, the display of user interface 2030 can be positioned at an angle relative to the housing 2010 and/or a top surface of the housing 2010.

Figure 18:
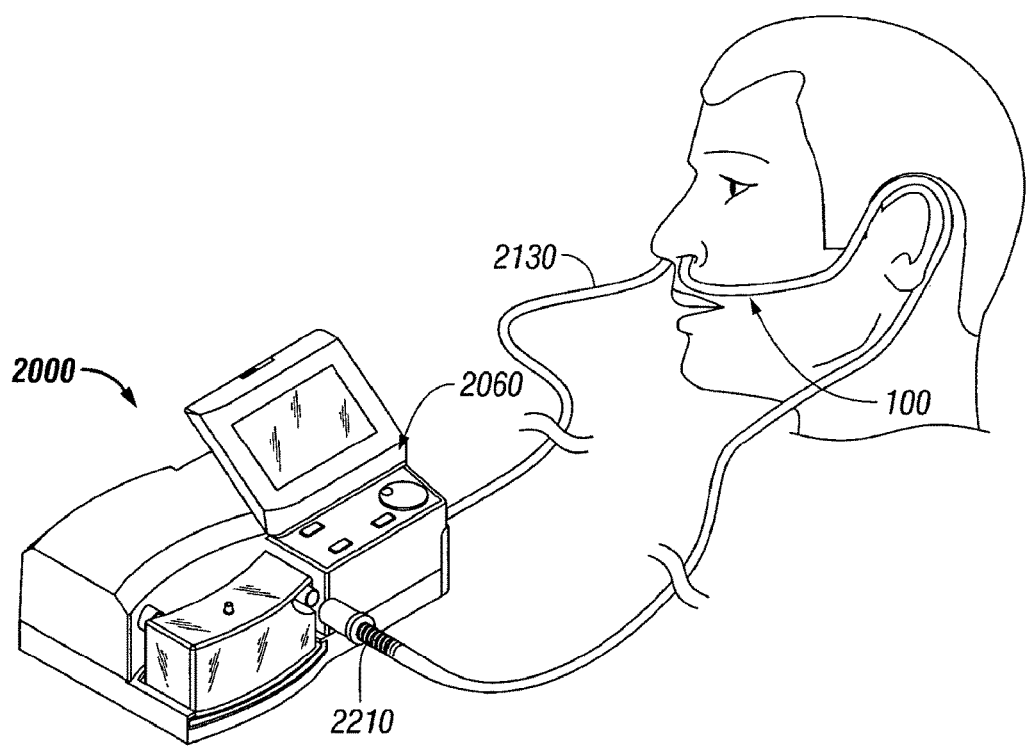
FIG. 18 illustrates a high flow therapy device including a nasal interface and a conduit in accordance with an embodiment of the present disclosure.
Figure 19:
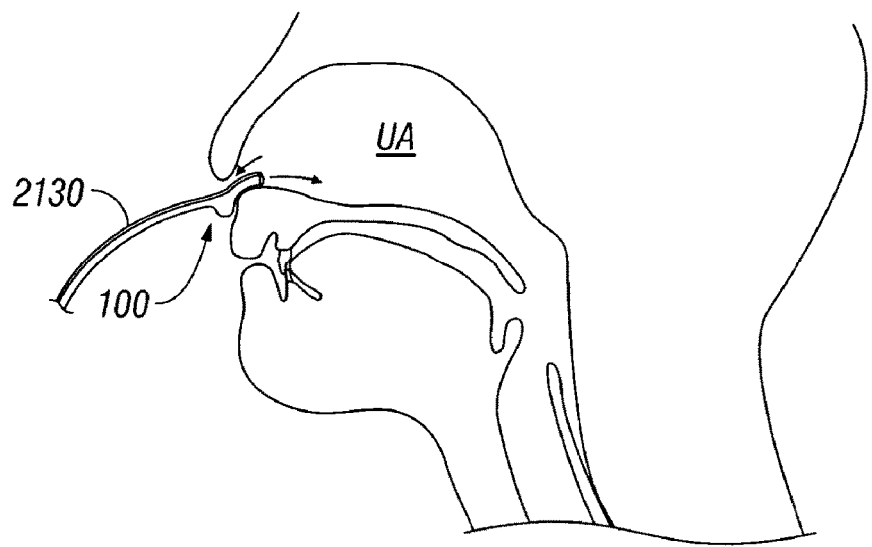
FIGS. 19 and 20 illustrate an enlarged view of a patient's upper airway and a nasal interface in accordance with two embodiments of the present disclosure.
Figure 20:
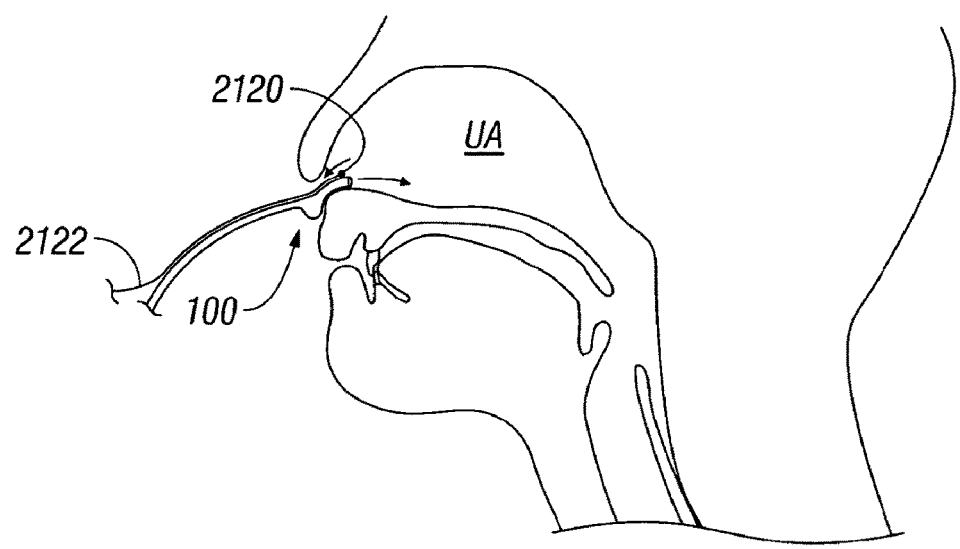

A heating element 2110 is shown schematically in FIG. 17 (and is hidden from view by humidity chamber 2020 in FIG. 15) is in electrical communication with microprocessor 2060 (which is included on printed circuit board ("PCB")), via wire 2112, for instance, and is capable of heating a liquid (e.g., water) within humidity chamber 2020 to create a gas. Non-sealing respiratory interface 100 is configured to delivery this gas to a patient. Further, a sensor 2120 or transducer (shown in FIG. 20) is disposed in electrical communication with microprocessor 2060 and is configured to measure pressure in the upper airway UA (including both the nasal cavity and the oral cavity) of a patient. In an embodiment, a sensor conduit 2130 extends between the upper airway of the patient and sensor 2120 (FIG. 19, sensor 2120 is not explicitly shown in FIG. 19, but may be disposed adjacent microprocessor 2060). In another embodiment, sensor 2120 is disposed at least partially within the upper airway of the patient with a wire 2122 relaying signals to microprocessor 2060 (FIGS. 18 and 20).

In use, a liquid (e.g., water) is inserted into humidity chamber 2020 through a chamber port 2022, for instance. Heating element 2110 heats the liquid to create a vapor or gas. This vapor heats and humidifies the gas entering humidity chamber 2020 through gas inlet port 2040. The heated and humidified vapor flows through gas outlet port 2050 and through non-sealing respiratory interface 100.

In a disclosed embodiment, sensor 2120 collects data for the measurement of the patient's respiration rate, tidal volume and minute volume. Further, based on measurements taken by sensor 2120 and relayed to microprocessor 2060, microprocessor 2060 is able to adjust the temperature of the gas, the humidity of the gas, the amount of oxygen of the gas, flow rate of the gas and/or the volume of the gas delivered to the patient. For example, if the pressure at the patient's upper airway is measured and determined to be too low (e.g., by a pre-programmed algorithm embedded on microprocessor 2060 or from a setting inputted by a operator), microprocessor 2060 may, for example, adjust the speed of blower 2080 and/or oxygen proportional valve 2100 so that sufficient pressure levels are maintained.

Additionally, sensor 2120 may be used to monitor respiratory rates, and microprocessor 2060 may signal alarms if the respiratory rate exceeds or falls below a range determined by either microprocessor 2060 or set by an operator. For example, a high respiratory rate alarm may alert the operator and may indicate that the patient requires a higher flow rate and/or higher oxygen flow.

With reference to FIG. 17, a pair of thermocouples 2200 and 2202 is illustrated, which detect the temperature entering and leaving a circuit 2210 disposed between non-sealing respiratory interface 100 and gas outlet port 2050. Further, a second heating element 2114 (or heater) (e.g., a heated wire) may be disposed adjacent air outlet port 2050 to further heat the gas. It is also envisioned that second heating element 2114 is disposed within circuit 2210. Thermocouples 2200 and 2202 are in communication with microprocessor 2060 and may be used to adjust the temperature of heating element 2110 and second heating element 2114. A feedback loop may be used to control the temperature of the delivered gas, as well as to control its humidity and to minimize rainout. FIG. 16 illustrates an embodiment of circuit 2210 including sensor conduit 2130 co-axially disposed therein, in accordance with an embodiment of the present disclosure.

Relating to the embodiment illustrated in FIG. 16, blower 2080 is used to draw in ambient air from air inlet port 2070 and force it through an air flow tube 2140, through gas inlet port 2040, through humidity chamber 2020 and through gas outlet port 2050 towards non-sealing respiratory interface 100. Blower 2080 is configured to provide a patient (e.g., an adult patient) with a gas flow rate of up to about 60 liters per minute. In a particular embodiment, it is envisioned that blower 2080 is configured to provide a patient with a gas flow rate of up to about 40 liters per minute. Additionally, an air intake filter 2072 (shown schematically in FIG. 17) may be provided adjacent air inlet port 2070 to filter the ambient air being delivered to the patient. It is envisioned that air intake filter 2072 is configured to reduce the amount of particulates (including dust, pollen, fungi (including yeast, mold, spores, etc.) bacteria, viruses, allergenic material and/or pathogens) received by blower 2080. Additionally, the use of blower 2080 may obviate the need for utilization of compressed air, for instance. It is also envisioned that a pressure sensor is disposed adjacent air intake filter 2072 (shown schematically in FIG. 17), which may be capable of determining when air intake filter 2072 should be replaced (e.g., it is dirty, it is allowing negative pressure, etc).

With continued reference to FIG. 16, oxygen inlet 2090 and is configured to connect to an external source of oxygen (or other gas) (not explicitly shown) to allow oxygen to pass through high flow therapy device 2000 and mix with ambient air, for instance. Proportion valve 2100, being in electrical communication with microprocessor 2060, is disposed adjacent oxygen inlet 2090 and is configured to adjust the amount of oxygen that flows from oxygen inlet 2090 through an oxygen flow tube 2150. As shown in FIGS. 16 and 17, oxygen flowing through oxygen flow tube 2150 mixes with ambient air (or filtered air) flowing through air flow tube 2140 in a mixing area 2155 prior to entering humidity chamber 2020.

In a disclosed embodiment, sensor 2120 measures both inspiration pressure and expiration pressure of the patient. In the embodiment illustrated in FIGS. 18 and 19, sensor conduit 2130 delivers the pressure measurements to sensor 2120 (not explicitly shown in FIGS. 18 and 19), which may be disposed adjacent microprocessor 2060. In the embodiment illustrated in FIG. 20, sensor 2120 is position adjacent the patient's upper airway and includes wire 2122 to transmit the readings to microprocessor 2060.

In various instances, clinicians do not desire ambient air to enter a patient's upper airway. To determine if ambient air is entering a patient's upper airway (air entrainment), the inspiration and expiration pressure readings from within (or adjacent) the upper airway may be compared to ambient air pressure. That is, a patient may be inhaling gas at a faster rate than the rate of gas that high flow therapy device 2000 is delivering to the patient. In such a circumstance (since non-sealing respiratory interface 100 is non-sealing), in addition to breathing in the supplied gas, the patient also inhales ambient air. Based on this information, microprocessor 2060 of high flow therapy device 2000 is able to adjust various flow parameters, such as increasing the flow rate, to minimize or eliminate the entrainment of ambient air.

Figure 21:
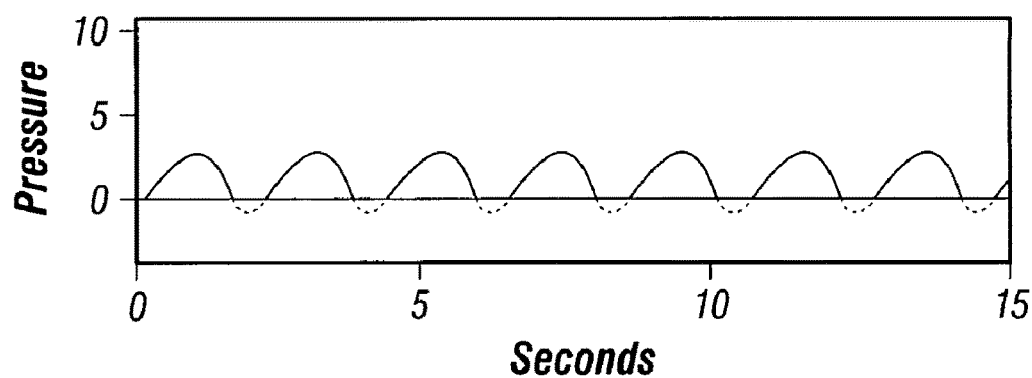
FIG. 21 illustrates an example of a screen shot of a user interface of the high flow therapy device of FIGS. 15-17 in accordance with an embodiment of the present disclosure.

FIG. 21 illustrates an example of a screen shot, which may be displayed on a display portion of user interface 2030. The crest of the sine-like wave represents expiration pressure and the valley represents inspiration pressure. In this situation, ambient air entrainment into the patient's upper airway is occurring as evidenced by the valley of the sine wave dipping below the zero-pressure line. Microprocessor 2060 may be configured to automatically adjust an aspect (e.g., increasing the flow rate) of the gas being supplied to the patient by high flow therapy device 2000 to overcome the entrainment of ambient air. Further, microprocessor 2060 may convey the pressure readings to the operator who may then input settings to adjust the flow rate to minimize entrainment of ambient air or to maintain a level of pressure above the ambient air pressure. Further, lowering the flow rates during expiration may also minimize oxygen flow through high flow therapy device 2000. Such lowering of a flow rate may also minimize entry of oxygen into a closed environment, such as the patient room or the interior of an ambulance, where high levels of oxygen might be hazardous.

In a disclosed embodiment, sensor conduit 2130 may be used as a gas analyzer, which may be configured to take various measurements (e.g., percent of oxygen, percentage of carbon dioxide, pressure, temperature, etc.) of air in or adjacent a patient's upper airway.

In another embodiment (not explicitly illustrated), a gas port may be disposed adjacent housing 2010 to communicate with exterior of housing 2010. It is envisioned that the gas port is configured to allow the use of external devices to measure various gas properties (e.g., percent oxygen and pressure). Additionally, the gas port may be used for external verification of gas values. Further, a communications port 2300, shown in FIG. 16, may be included to facilitate connection with an external device, such as a computer, for additional analysis, for instance. Further, communications port 2300 enables connection with another device, enabling data to be monitored distantly, recorded and/or reprogrammed, for example.

A directional valve 2160 and/or a sample pump 2170 (schematically shown in FIG. 17) may also be included to facilitate sampling the gas for analysis. More specifically, in a particular embodiment, sample pump 2170 is capable of moving a quantity of gas towards the gas analyzer. As shown schematically in FIG. 17, the gas sample can be taken from a patient's upper airway via sensor conduit 2130 or from mixing area 2155 via a sample line 2180 and a sample port 2182 (FIG. 16). Directional valve 2160 may be controlled by microprocessor 2060 to direct a gas sample from either location (or a different location such as after the gas is heated). The gas analyzer can compare measurements of the gas sample(s) with predetermined measurements to ensure high flow therapy device 2000 is working optimally. It is further envisioned that sample pump 2170 may be configured to pump a gas or liquid towards the patient to provide the patient with an additional gas, such as an anesthetic, for instance and/or to clean or purge sensor conduit 2130.

The present disclosure also relates to methods of supplying a patient with gas. The method includes providing high flow therapy device 2000, as described above, for example, heating the gas, and delivering the gas to the patient. In this embodiment, high flow therapy device 2000 includes microprocessor 2060, heating element 2110 disposed in electrical communication with microprocessor 2060, non-sealing respiratory interface 100 configured to deliver gas to the patient and sensor 2120 disposed in electrical communication with microprocessor 2060 and configured to measure pressure in the upper airway of the patient. The method of this embodiment may be used, for instance, to provide a patient with respiratory assistance. Blower 2080 may also be included in high flow therapy device 2000 of this method. Blower 2080 enables ambient air to enter high flow therapy device 2000 (e.g., through filter 2072) and be supplied to the patient. In such an embodiment, high flow therapy device is portable, as it does not need an external source of compressed air, for example.

Another method of the present disclosure relates to minimizing respiratory infections of a patient. In an embodiment of this method, high flow therapy device 2000 includes heating element 2110 and non-sealing respiratory interface 100. Here, a patient may be provided with heated and/or humidified air (e.g., at varying flow rates) to help minimize respiratory infections of the patient. Further, such a method may be used in connection with certain filters 2072 to help prevent patients from obtaining various conditions associated with inhaling contaminated air, such as in a hospital. Additionally, providing appropriately warmed and humidified respiratory gases optimizes the motion of the cilia that line the respiratory passages from the anterior third of the nose to the beginning of the respiratory bronchioles, further minimizing risk of infection. Further, supplemental oxygen may add to this effect. Microprocessor 2060 in connection with sensor 2120 may also be included with high flow therapy device 2000 of this method for measuring and controlling various aspects of the gas being delivered to the patient, for instance, as described above.

A further method of the present disclosure relates to another way of supplying a patient with gas. The present method includes providing high flow therapy device 2000 including heating element 2110, non-sealing respiratory interface 100, blower 2080, air inlet port 2070 configured to enable ambient air to flow towards blower 2080 and filter 2070 disposed in mechanical cooperation with air inlet port 2070 and configured to remove pathogens from the ambient air. High flow therapy device 2000 of this method may also include microprocessor 2060 and sensor 2120.

Another method of the present disclosure includes the use of high flow therapy device 2000 to treat headaches, upper airway resistance syndrome, obstructive sleep apnea, hypopnea and/or snoring. High flow therapy device 2000 may be set to provide sufficient airway pressure to minimize the collapse of the upper airway during inspiration, especially while the use is asleep. HFT may be more acceptable to children and other who may not tolerate traditional CPAP therapy, which requires a sealing interface. Early treatment with HFT may prevent the progression of mild upper airway resistance syndrome to more advanced conditions such as sleep apnea and its associated morbidity.

Another method of the present disclosure is the treatment of headaches using HFT. In an embodiment of treating/preventing headaches, gas may be delivered to patient at a temperature of between about 32.degree. C. and about 40.degree. C. (temperature in the higher end of this range may provide a more rapid response) and having at least about 27 milligrams of water vapor per liter. More specifically, it is envisioned that a gas having a water vapor content of between about 33 mg/liter and about 44 mg/liter may be used. It is envisioned that the gas being delivered to the patient includes moisture content that is similar to that of a typical exhaled breath. In an embodiment, the flow rates of this heated and humidified air are sufficient to prevent/minimize entrainment of ambient air into the respired gas during inspiration, as discussed above. The inclusion of an increased percentage of oxygen may also be helpful. Further, the gas may be delivered to the patient using non-sealing respiratory interface 100.

High flow therapy device 2000 used in these methods includes heating element 2110 and non-sealing respiratory interface 100. Microprocessor 2060 and sensor 2120 may also be included in high flow therapy device 2000 of this method. The inclusion of blower 2080, in accordance with a disclosed embodiment, enables high flow therapy device 2000 to be portable, as it does not need to be connected to an external source of compressed air or oxygen. Thus, high flow therapy device 2000 of this method is able to be used, relatively easily, in a person's home, a doctor's office, an ambulance, etc.

The present disclosure also relates to a method of delivering respiratory gas to a patient and includes monitoring the respiratory phase of the patient. Monitoring of a patient's respiratory phase is enabled by taking measurements of pressure in a patient's upper airway. Additionally, respiratory phase may be determined by pressure with circuit 2210 or by monitoring activity of the phrenic nerve. Real-time pressure measurements (see sine-like wave in FIG. 21, for example) enable real-time supplying of gas at different pressures to be delivered to the patient, or variable pressure delivery. For example, gas at a higher pressure may be delivered to the patient during inspiration and gas at a lower pressure may be delivered to the patient during expiration. This example may be useful when a patient is weak and has difficulty exhaling against an incoming gas at a high pressure. It is further envisioned that the pressure level of the gas being delivered to a patient is gradually increased (e.g., over several minutes) to improve patient comfort, for instance.

Figure 22:
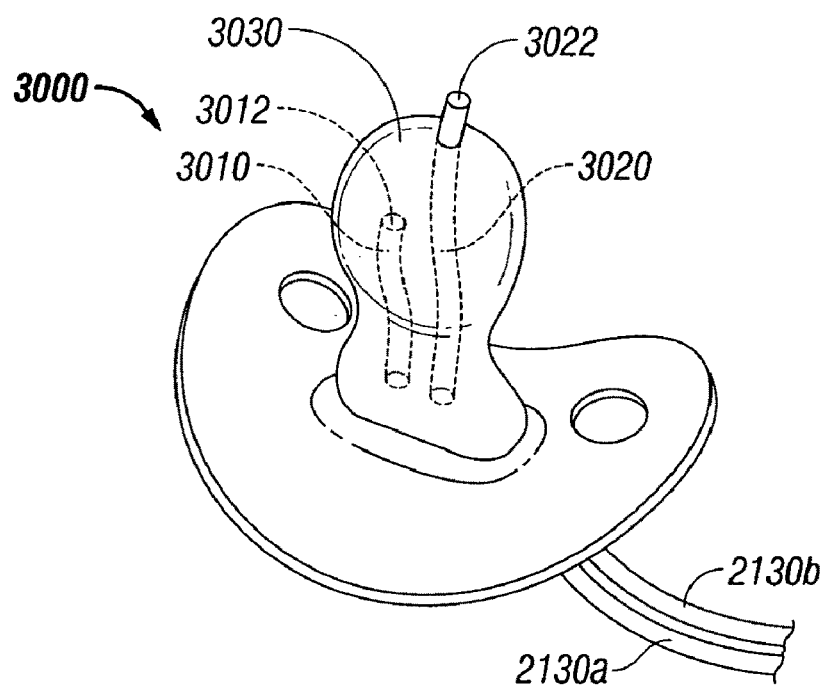
FIGS. 22 and 23 illustrate examples of a non-sealing respiratory interface in the form of a mouthpiece in accordance with embodiments of the present disclosure.
Figure 23:
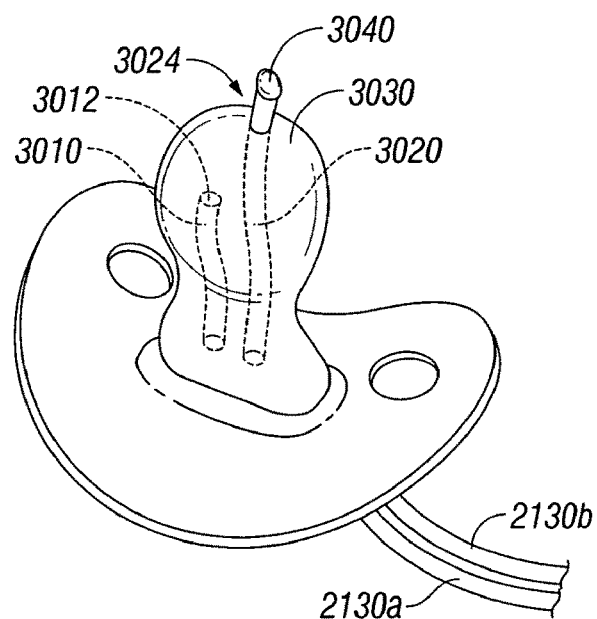
Figure 24:
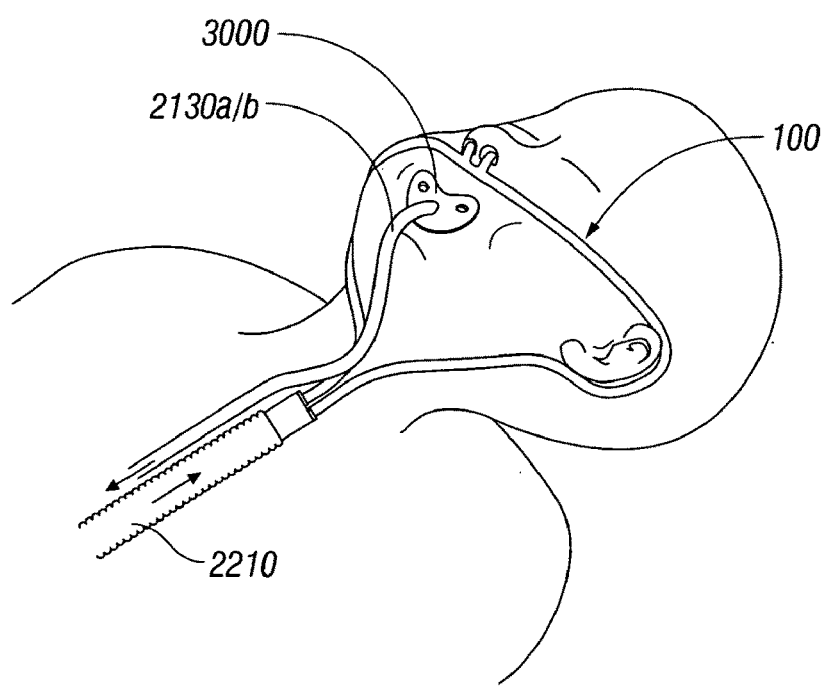
FIG. 24 illustrates a mouthpiece of FIG. 22 or 23 in use on a patient in accordance with an embodiment of the present disclosure.

With reference to FIGS. 22-24, mouthpiece 3000 is illustrated in accordance with an embodiment of the present disclosure. As briefly described above, mouthpiece 3000 is an example of a respiratory interface of the present disclosure. Mouthpiece 3000 (illustrated resembling a pacifier) may be used to detect upper airway pressure of a patient.

A first mouthpiece port 3010 may be used to measure pressure inside mouthpiece 3000 through open end 3012 of first port. First mouthpiece port 3010 may include an open-ended tube that communicates the pressure with mouthpiece 3000 to sensor 2120 (not explicitly shown in FIGS. 22-24) via first port conduit 2130a. Sensor 2120 may also be positioned within mouthpiece 3000. It is envisioned that mouthpiece 3000 is at least partially filled with a gas or liquid, e.g., water.

The pressure within mouthpiece 3000 may help evaluate, record or otherwise use the pressure data for determining the strength of sucking or feeding, for instance. The timing of the sucking motion and the differential pressures in the mouth may also be measured. The sucking pressure may be used to help determine the strength of the sucking and may be used to evaluate the health of an infant, for instance. The measurement of oral-pharyngeal pressure may also give data for setting or adjusting respiratory support therapy for the patient. It is envisioned that a relatively short first mouthpiece port 3010 may be used so that a bulb 3030 of mouthpiece 3000 acts as a pressure balloon. It is also envisioned that a relatively long first mouthpiece port 3010 having rigidity may be used to help prevent closure of the tube from pressure from alveolar ridges or from teeth, for example.

A second mouthpiece port 3020 is configured to enter a patient's mouth or oral cavity when mouthpiece 3000 is in use and is configured to measure pressure within the oral cavity (upper airway pressure) through an open end 3022 of second mouthpiece port 3020. Pressure from within the upper airway (e.g., measured adjacent the pharynx) may be transmitted to sensor 2120 via second port conduit 2130b or sensor 2120 may be positioned adjacent mouthpiece 3000. That is, the pressure communicated from with the upper airway to the patient's mouth is the pressure being measured. It is envisioned that second mouthpiece port 3020 extends beyond a tip of bulb 3030 to facilitate the acquisition of an accurate upper airway pressure measurement.

Referring to FIG. 23, a balloon 3040 is shown adjacent a distal end 3024 of second port 3020. Here, it is envisioned that a lumen of conduit 2130b is in fluid communication with the internal area of balloon 3040. Further, any forces against a wall of balloon 3040 are transmitted through the lumen towards sensor 2120 or transducer for control, observation or analysis.

The pressure within the oral cavity may vary during the phases of sucking and swallowing. High flow therapy device 2000 using mouthpiece 3000 enables concurrent measurement of sucking pressure within mouthpiece 3000 and the pressure outside mouthpiece 3000. This data may help determine treatment characteristics for respiratory support for infants, children or adults, e.g., unconscious adults.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. For example, although the embodiment shown in FIG. 1 shows each nozzle 125, 130 having a two conduit inlets 152, 154, in alternative embodiments of the invention, one or more of the nozzles 125, 130 may have more or less than two conduit inlets (and/or more or less than two sensors). Further, sensor 2120 may be situated or in communication with any area of the airway, and is not limited to sensing the environment of the anterior nares. Although specific terms are employed herein, they are used in a generic and descriptive sense only and not for purposes of limitation.

We claim:

1. A high flow therapy system for delivering heated and humidified respiratory gas to an airway of a patient, the system comprising:
   a microprocessor;
   a respiratory gas flow pathway for delivering the respiratory gas to the airway of the patient by way of a non-sealing respiratory interface, wherein flow rate of the respiratory gas is controlled by the microprocessor;
   a mixing area for mixing oxygen and air in the respiratory gas flow pathway;

a humidification area downstream of the mixing area and configured for humidifying respiratory gas in the respiratory gas flow pathway; and a heated delivery conduit for minimizing condensation of humidified respiratory gas;

wherein the non-sealing respiratory interface is configured to form a passageway for exhaled gas of the patient to pass to ambient atmosphere without passing through a remainder of the system, wherein the non-sealing respiratory interface includes:
a tubular base portion;
at least one nozzle defining at least one inlet; and
at least one outlet member defining an outlet, the at least one outlet member being substantially parallel to the at least one nozzle, the at least one outlet member and the at least one nozzle positioned on opposite sides of the base portion,
wherein the at least one inlet is in gaseous communication with the outlet.

2. The high flow therapy system of claim 1, wherein at least one of respiration rate, tidal volume and minute volume are calculated by the microprocessor.

3. The high flow therapy system of claim 1, wherein the microprocessor is configured to control at least one of temperature of the gas, humidity of the gas, mixture of the gas, the flow rate of the gas, and volume of the gas delivered to the patient.

4. The high flow therapy system of claim 1, wherein the microprocessor is configured to adjust flow rates based on at least one of a pre-programmed algorithm and a setting inputted by an operator.

5. The high flow therapy system of claim 1, wherein the system is configured to signal an alarm when conditions deviate from pre-determined criteria.

6. The high flow therapy system of claim 1, wherein the system is configured to control the flow rate of the respiratory gas delivered to the patient based on a respiratory phase of the patient during use.

7. The high flow therapy system of claim 1, wherein the system is configured to deliver the respiratory gas to the patient at different airway pressures based on a respiratory phase of the patient during use.

8. The high flow therapy system of claim 1, further comprising a gas analyzer.

9. The high flow therapy system of claim 1, further comprising a display.

10. The high flow therapy system of claim 1, further comprising a proportional valve.

11. The high flow therapy system of claim 1, wherein the non-sealing respiratory interface includes a nasal cannula.

12. The high flow therapy system of claim 1, further comprising a gas inlet configured to connect to an external source of gas.

13. The high flow therapy system of claim 1, wherein the non-sealing respiratory interface includes at least one conduit configured to extend from the inlet through the at least one nozzle, through the base portion, and to the outlet.

14. The high flow therapy system of claim 1, wherein the at least one inlet is connected to a conduit that is configured to route gas to a sensor.

15. The high flow therapy system of claim 1, wherein the at least one inlet includes:
a first inlet that is connected to a first conduit configured to route gas to a first sensor; and
a second inlet that is connected to a second conduit configured to route gas to a second sensor, wherein the second conduit is physically separate from the first conduit.

16. The high flow therapy system of claim 1, wherein the outlet is located at an end of the at least one outlet member.

17. The high flow therapy system of claim 1, wherein the at least one outlet member is configured to connect to a sensor via accessory tubing.

18. The high flow therapy system of claim 1, further comprising a blower.

19. The high flow therapy system of claim 18, wherein the blower is configured for providing a patient with gas flow rates of up to 60 liters per minute.

20. The high flow therapy system of claim 1, wherein the non-sealing respiratory interface includes a sensor mounted thereon configured to measure a pressure in the airway of the patient, and wherein the sensor is configured to monitor the airway of the patient.

21. The high flow therapy system of claim 20, wherein the sensor communicates information on the monitored airway of the patient to the microprocessor.

22. The high flow therapy system of claim 20, wherein the sensor is configured to measure at least one of inspiration pressure and expiration pressure of the patient.

23. The high flow therapy system of claim 20, wherein the sensor is at least partially enclosed within the respiratory gas flow pathway.

24. A high flow therapy system for delivering heated and humidified respiratory gas to an airway of a patient, the system comprising:
a microprocessor;
a respiratory gas flow pathway for delivering the respiratory gas to the airway of the patient by way of a non-sealing respiratory interface, wherein flow rate of the respiratory gas is controlled by the microprocessor;
a blower controlled by the microprocessor;
a mixing area for mixing a first gas and a second gas in the respiratory gas flow pathway;
a humidification area downstream of the mixing area and for humidifying respiratory gas in the respiratory gas flow pathway; and
a heated delivery conduit for minimizing condensation of humidified respiratory gas; and wherein the non-sealing respiratory interface is configured to form a passageway for exhaled gas of the patient to pass to ambient atmosphere without passing through a remainder of the system.
wherein the non-sealing respiratory interface includes:
a tubular base portion;
at least one nozzle defining at least one inlet; and
at least one outlet member defining an outlet, the at least one outlet member being substantially parallel to the at least one nozzle, the at least one outlet member and the at least one nozzle positioned on opposite sides of the base portion,
wherein the at least one inlet is in gaseous communication with the outlet.

25. A high flow therapy system for delivering heated and humidified respiratory gas to an airway of a patient, the system comprising:
a microprocessor;
a respiratory gas flow pathway for delivering the respiratory gas to the airway of the patient by way of a non-sealing respiratory interface, wherein flow rate of the respiratory gas is controlled by the microprocessor located within a housing;

a mixing area located within the housing for mixing a first gas and a second gas in the respiratory gas flow pathway;
a humidification area downstream of the mixing area and located outside of the housing for humidifying respiratory gas in the respiratory gas flow pathway;
a heating element in thermal communication with the humidification area; and
a heated delivery conduit for minimizing condensation of humidified respiratory gas; wherein the non-sealing respiratory interface is configured to form a passageway for exhaled gas of the patient to pass to ambient atmosphere without passing through a remainder of the system.
wherein the non-sealing respiratory interface includes:
 a tubular base portion;
 at least one nozzle defining at least one inlet; and
 at least one outlet member defining an outlet, the at least one outlet member being substantially parallel to the at least one nozzle, the at least one outlet member and the at least one nozzle positioned on opposite sides of the base portion,
 wherein the at least one inlet is in gaseous communication with the outlet.

* * * * *